United States Patent
Lo et al.

(10) Patent No.: US 12,190,998 B2
(45) Date of Patent: *Jan. 7, 2025

(54) COMBINED SIZE- AND COUNT-BASED ANALYSIS OF MATERNAL PLASMA FOR DETECTION OF FETAL SUBCHROMOSOMAL ABERRATIONS

(71) Applicant: The Chinese University of Hong Kong, Hong Kong (CN)

(72) Inventors: Yuk-Ming Dennis Lo, Hong Kong SAR (CN); Rossa Wai Kwun Chiu, Hong Kong SAR (CN); Kwan Chee Chan, Hong Kong SAR (CN); Peiyong Jiang, Hong Kong SAR (CN); Cheuk Yin Jandy Yu, Hong Kong SAR (CN)

(73) Assignee: The Chinese University of Hong Kong, New Territories (HK)

( * ) Notice: Subject to any disclaimer, the term of this patent is extended or adjusted under 35 U.S.C. 154(b) by 1154 days.

This patent is subject to a terminal disclaimer.

(21) Appl. No.: 16/387,049

(22) Filed: Apr. 17, 2019

(65) Prior Publication Data

US 2019/0244679 A1    Aug. 8, 2019

Related U.S. Application Data

(63) Continuation of application No. 14/994,023, filed on Jan. 12, 2016, now Pat. No. 10,319,463.

(60) Provisional application No. 62/107,227, filed on Jan. 23, 2015.

(51) Int. Cl.
| | | |
|---|---|---|
| *G16B 20/10* | (2019.01) | |
| *C12Q 1/6883* | (2018.01) | |
| *G16B 20/00* | (2019.01) | |
| *G16B 20/20* | (2019.01) | |
| *G16B 30/00* | (2019.01) | |
| *G16B 40/00* | (2019.01) | |

(52) U.S. Cl.
CPC .......... *G16B 20/10* (2019.02); *C12Q 1/6883* (2013.01); *G16B 20/00* (2019.02); *G16B 20/20* (2019.02); *G16B 30/00* (2019.02); *G16B 40/00* (2019.02)

(58) Field of Classification Search
CPC ........ G06N 7/005; G06N 3/08; G06N 3/0472; C12Q 1/6869; C12Q 1/6827; C12Q 2537/165; C12Q 1/68; C12Q 2537/16; C12Q 2545/114; C12Q 1/6837; C12Q 2537/143; C12Q 2600/156; C12Q 1/6883; C12Q 1/6809; C12Q 2600/172; G16B 30/00; G16B 20/00; G16B 30/10; G16B 20/20; G16B 40/00; G16B 40/20; G16B 20/10; G16B 15/00; G16B 50/00; G16B 25/00; G16B 30/20; G16B 50/30; G16B 45/00; G16B 5/20; G16B 50/20; G16B 25/30; G16H 50/20; G16H 50/30; G16H 10/40; G16H 10/60; G16H 50/70; G16H 70/20; G16H 70/60; G16H 50/50; G06K 9/6267; G06K 9/62; G06K 9/6297; G06K 9/6298; G06K 9/6296; G06K 9/6231; G06K 9/6255; G06K 9/626; G01N 2800/387; G01N 2800/385; G06F 18/00; G06F 18/295; G06F 18/20; G06F 18/22; G06F 18/24
See application file for complete search history.

(56) References Cited

U.S. PATENT DOCUMENTS

| | | |
|---|---|---|
| 8,620,593 B2 | 12/2013 | Lo et al. |
| 8,706,422 B2 | 4/2014 | Lo et al. |
| 2009/0029377 A1 | 1/2009 | Lo et al. |
| 2013/0237431 A1 | 9/2013 | Lo et al. |
| 2013/0267425 A1 | 10/2013 | Liao et al. |
| 2014/0195164 A1 | 7/2014 | Lo et al. |
| 2014/0227699 A1 | 8/2014 | Lo et al. |

FOREIGN PATENT DOCUMENTS

| | | |
|---|---|---|
| CN | 101849236 A | 9/2010 |
| CN | 103003447 | 3/2013 |
| CN | 103403182 | 11/2013 |
| CN | 104232777 A | 12/2014 |
| CN | 104254618 | 12/2014 |
| WO | 2009013496 A1 | 1/2009 |
| WO | 2009051842 | 4/2009 |
| WO | 2014107765 A1 | 7/2014 |

(Continued)

OTHER PUBLICATIONS

Venkatraman et al. (2007) A faster circular binary segmentation algorithm for the analysis of array CGH data. Bioinformatics vol. 23 No. 6 p. 657-663. (Year: 2007).*

(Continued)

*Primary Examiner* — Mary K Zeman

(74) *Attorney, Agent, or Firm* — Kilpatrick Townsend & Stockton LLP

(57) ABSTRACT

An aberration in a fetal genome can be identified by analyzing a sample of fetal and maternal DNA. Classifications of whether an aberration (amplification or deletion) exists in a subchromosomal region are determined using count-based and size-based methods. The count classification and the size classification can be used in combination to determine whether only the fetus or only the mother, or both, have the aberration in the subchromosomal region, thereby avoiding false positives when the mother has the aberration and the fetus does not.

22 Claims, 11 Drawing Sheets

(56) References Cited

FOREIGN PATENT DOCUMENTS

| WO | 2014190286 | 11/2014 |
|---|---|---|
| WO | 2016112850 | 7/2016 |

OTHER PUBLICATIONS

DNACopy: a package for analyzing DNA copy number data. (Oct. 13, 2014) Bioconductor R package . (Year: 2014).*
Sehnert, A. J. et al. Optimal Detection of Fetal Chromosomal Abnormalities by Massively Parallel DNA sequencing of Cell-Free Fetal DNA from Maternal Blood. 2011 Clinical Chemistry, 57:7 1042-1049; (Year: 2011).*
Chen, S. et al (2013) a method for noninvasive detection of fetal large deletions/ duplications by low coverage massively parallel sequencing. Prenatal Diagnosis 33: 584-590. (Year: 2013).*
Examination Report No. 1 dated Feb. 18, 2021 in AU Patent Application No. 2016208914. 5 pages.
Extended European Search Report dated Dec. 20, 2019 in EP Patent Application No. 19192638.5. 18 pages.
English translation of Office Action and Search Report mailed Aug. 14, 2020 in TW Patent Application No. 105102115. 5 pages.
U.S. Appl. No. 14/994,023, "Non-Final Office Action," Jul. 24, 2018, 11 pages.
U.S. Appl. No. 14/994,023, "Notice of Allowability," Apr. 8, 2019, 5 pages.
U.S. Appl. No. 14/994,023, "Notice of Allowance," Jan. 14, 2019, 7 pages.
Chan et al., "Size Distributions of Maternal and Fetal DNA in Maternal Plasma," Clinical Chemistry, vol. 50, Issue 1, Jan. 2004, pp. 88-92.
EP16739780.1, "Extended European Search Report," May 22, 2018, 17 pages.
Lo et al., "Maternal Plasma DNA Sequencing Reveals the Genome-Wide Genetic and Mutational Profile of the Fetus," Science Translation Medicine, vol. 2, No. 61, 61ra91, Dec. 8, 2010, pp. 1-13.
PCT/CN2016/071357, "International Search Report and Written Opinion," Apr. 29, 2016, 12 pages.
Sehnert et al., "Optimal Detection of Fetal Chromosomal Abnormalities by Massively Parallel DNA Sequencing of Cell-Free Fetal DNA from Maternal Blood," Clinical Chemistry, vol. 57, No. 7, 2011, pp. 1042-1049.
Srinivasan et al., "Noninvasive Detection of Fetal Subchromosome Abnormalities Via Deep Sequencing of Maternal Plasma," The American Journal of Human Genetics, vol. 92, Issue 2, Feb. 7, 2013, pp. 167-176.
Yu et al., "Combined Count- And Size-Based Analysis Of Maternal Plasma DNA For Noninvasive Prenatal Detection Of Fetal Subchromosomal Aberrations Facilitates Elucidation Of The Fetal And/Or Maternal Origin Of The Aberrations," Clinical Chemistry, vol. 63, No. 2, Dec. 14, 2016, pp. 495-502.
Yu et al., "Noninvasive Prenatal Molecular Karyotyping from Maternal Plasma," PLoS One, vol. 8(4), Apr. 2013, 8 pages.
Yu et al., "Size-Based Molecular Diagnostics Using Plasma DNA For Noninvasive Prenatal Testing," Proceedings of The National Academy of Sciences, vol. 111, No. 23, Jun. 10, 2014, pp. 8583-8588.
Extended European Search Report dated Jan. 29, 2024 in EP Patent Application No. 23200807.8. 16 pages.
Chiu, Rossa W.K. et al.; "Non-invasive prenatal diagnosis by single molecule counting technologies"; 2009; Trends in Genetics; vol. 25, No. 7; pp. 324-331.
English translation of Office Action and Search Report mailed Aug. 12, 2024 in TW Patent Application No. 112149975. 5 pages.
Chan, Landon L et al.; "Bioinformatics analysis of circulating cell-free DNA sequencing data"; Clinical Biochemistry; 2015; vol. 48, No. 15; pp. 962-975.

* cited by examiner

| Mother | Fetus | Count-based | Size-based |
|---|---|---|---|
| duplication | duplication | Over-represented | Normal |
| deletion | deletion | Under-represented | Normal |
| Normal | duplication | Over-represented | Shorter |
| Normal | deletion | Under-represented | Longer |
| duplication | Normal | Over-represented | Longer |
| deletion | Normal | Under-represented | Shorter |

FIG. 1

| Mother | Fetus | Count-based z-score | $F_{CNA}$ | Size-based z-score |
|---|---|---|---|---|
| Normal | Copy number gain | ⇐ | < 50 % | ⇐ |
| Normal | Copy number loss | ⇒ | < 50 % | ⇒ |
| Copy number gain | Copy number gain | ⇐ ⇒ | > 50 % | Normal |
| Copy number loss | Copy number loss | ⇐ ⇒ | > 50 % | Normal |
| Copy number gain | Normal | ⇐ ⇒ | > 50 % | ⇒ |
| Copy number loss | Normal | ⇐ ⇒ | > 50 % | ⇐ |

FIG. 4

| Case | Genomic coordinates of the copy number aberration(s) detected by the tag counting method (size) | Count-based z-scores | Size-based z-score |
|---|---|---|---|
| 01 | Chr22: 17,000,000 – 20,000,000 (3 Mb) | -3.7 to -8.3 | -4.22 |
| 02 | Chr22: 17,000,000 – 20,000,000 (3 Mb) | -7.3 to -13.2 | -5.76 |
| 03 | Chr22: 17,000,000 – 20,000,000 (3Mb) | -5.2 to -9.6 | -6.56 |
| 04 | Chr22: 17,000,000 – 20,000,000 (3 Mb) | 6.8 to 13.0 | 6.95 |
| 05 | Chr3: 194,000,000 – 199,000,000 (5 Mb) | 39.7 to 71.7 | 0.34 |
| 06 | Chr4: 158,000,000 – 189,000,000 (31 Mb) | 3.2 to 10.8 | 8.10 |
| | | -3.8 to -12.3 | -14.40 |

FIG. 5

| Case | Gestational age (weeks) | Aberrations | Mother | Fetus |
|---|---|---|---|---|
| M10219[a] | 12 3/7 | 2.4 Mb gain on chr22 (confirmed by array CGH[b]) | Absent | Present |
| HK310[a] | 22 5/7 | Microdeletion on 22q11.2 (confirmed by QF-PCR & FISH) | Absent | Present |
| M14-13489-F1 | 12 2/7 | 1.6 Mb gain on chr4 (confirmed by array CGH[b]) | Present | Absent |
| DNA11-04530 | 14 | 1.33 Mb loss on chr4 (confirmed by array CGH[b]) | Present | Absent |
| PW503[a] | 20 2/7 | 2.4 Mb gain on chr22 (confirmed by array CGH[b]) | Present | Present |
| M11879 | 22 5/7 | 3.5 Mb gain on chr12 (confirmed by array CGH[b]) | Present | Present |

[a]Cases that have been included in a previous study (7).

[b]Array CGH, array comparative genomic hybridization.

FIG. 6

| Case | Genomic coordinates of the tested regions (size of the region) | Count-based z-score | Size-based z-score |
|---|---|---|---|
| M10219 | Chr4: 60,000,000 - 62,000,000 (2 Mb) | 0.84 | -1.31 |
| | Chr4: 97,000,000 - 99,000,000 (2 Mb) | 0.56 | -2.05 |
| | Chr12: 12,000,000 - 16,000,000 (4 Mb) | 0.41 | 0.07 |
| HK310 | Chr4: 60,000,000 - 62,000,000 (2 Mb) | 0.28 | 1.95 |
| | Chr4: 97,000,000 - 99,000,000 (2 Mb) | -0.00 | 1.05 |
| | Chr12: 12,000,000 - 16,000,000 (4 Mb) | 0.66 | 0.28 |
| M14-13489-F1 | Chr4: 97,000,000 - 99,000,000 (2 Mb) | 0.04 | -0.45 |
| | Chr12: 12,000,000 - 16,000,000 (4 Mb) | -0.04 | -1.26 |
| | Chr22: 17,000,000 - 20,000,000 (3 Mb) | 6.61 | -0.82 |
| DNA11-04530 | Chr4: 60,000,000 - 62,000,000 (2 Mb) | 1.92 | -2.69 |
| | Chr12: 12,000,000 - 16,000,000 (4 Mb) | -2.28 | 0.74 |
| | Chr22: 17,000,000 - 20,000,000 (3 Mb) | -0.68 | 2.63 |
| PW503 | Chr4: 60,000,000 - 62,000,000 (2 Mb) | 2.69 | -1.20 |
| | Chr4: 97,000,000 - 99,000,000 (2 Mb) | 0.12 | -1.34 |
| | Chr12: 12,000,000 - 16,000,000 (4 Mb) | 0.19 | -0.80 |
| M11879 | Chr4: 60,000,000 - 62,000,000 (2 Mb) | -0.42 | -2.02 |
| | Chr4: 97,000,000 - 99,000,000 (2 Mb) | 0.55 | 0.24 |

FIG. 8

COMBINED SIZE- AND COUNT-BASED ANALYSIS OF MATERNAL PLASMA FOR DETECTION OF FETAL SUBCHROMOSOMAL ABERRATIONS

CROSS-REFERENCES TO RELATED APPLICATIONS

The present application is a continuation of U.S. application Ser. No. 14/994,023, entitled "COMBINED SIZE- AND COUNT-BASED ANALYSIS OF MATERNAL PLASMA FOR DETECTION OF FETAL SUBCHROMOSOMAL ABERRATIONS," filed Jan. 12, 2016, which claims priority from and is a nonprovisional application of U.S. Provisional Application No. 62/107,227, entitled "Combined Size- and Count-Based Analysis Of Maternal Plasma For Detection Of Fetal Subchromosomal Aberrations," filed Jan. 23, 2015, the entire contents of which are herein incorporated by reference for all purposes. This application is also related to U.S. Patent Publication 2009/0029377, entitled "Diagnosing Fetal Chromosomal Aneuploidy Using Massively Parallel Genomic Sequencing," by Lo et al., filed Jul. 23, 2008; and U.S. Pat. No. 8,620,593, entitled "Size-Based Genomic Analysis," by Lo et al., filed Nov. 5, 2010, the disclosures of which are incorporated by reference in their entirety for all purposes.

BACKGROUND

Cell-free DNA in maternal plasma comprises a mixture of fetal and maternal DNA. Noninvasive prenatal measurements of maternal plasma can be used to detect subchromosomal copy number aberrations (CNAs) by counting DNA fragments from subchromosomal regions. But, the counting does not distinguish fetal DNA from maternal DNA. Therefore, aberrations detected by counting DNA fragments could be derived from the fetus or the mother. Thus, when a mother herself is a carrier of a CNA, one could not discern if her fetus has inherited the CNA. In addition, false-positive results would become more prevalent when more subchromosomal regions are analyzed.

Embodiments can address these and other problems.

BRIEF SUMMARY

Embodiments use a strategy that combines count-based and size-based analyses of maternal samples including maternal and fetal DNA for the detection of fetal subchromosomal copy number aberrations (CNAs). CNAs in regions can be detected using a count-based analysis. A size-based analysis of the DNA molecules can also be used to analyze regions determined to have a CNA, where the size-based analysis can be used to distinguish between aberrations that originate from the fetus or the mother, or from both.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 1 shows a table 100 of six scenarios for combinations of count-based and size-based outcomes according to embodiments of the present invention.

FIG. 4 shows a table 400 of the six scenarios for combinations of count-based and size-based outcomes along with $F_{CNA}$ values according to embodiments of the present invention.

FIG. 5 is a table 500 showing count-based scores and size-base scores for six maternal plasma DNA samples for illustrating accuracy of embodiment of the present invention.

FIG. 6 is a table 600 showing information about six cases with CNAs derived from either the fetus or the mother, or both.

FIG. 8 is a table 800 showing count-based and size-based z-scores of the tested regions with no detectable CNAs in each case according to embodiments of the present invention.

TERMS

Figure 2:
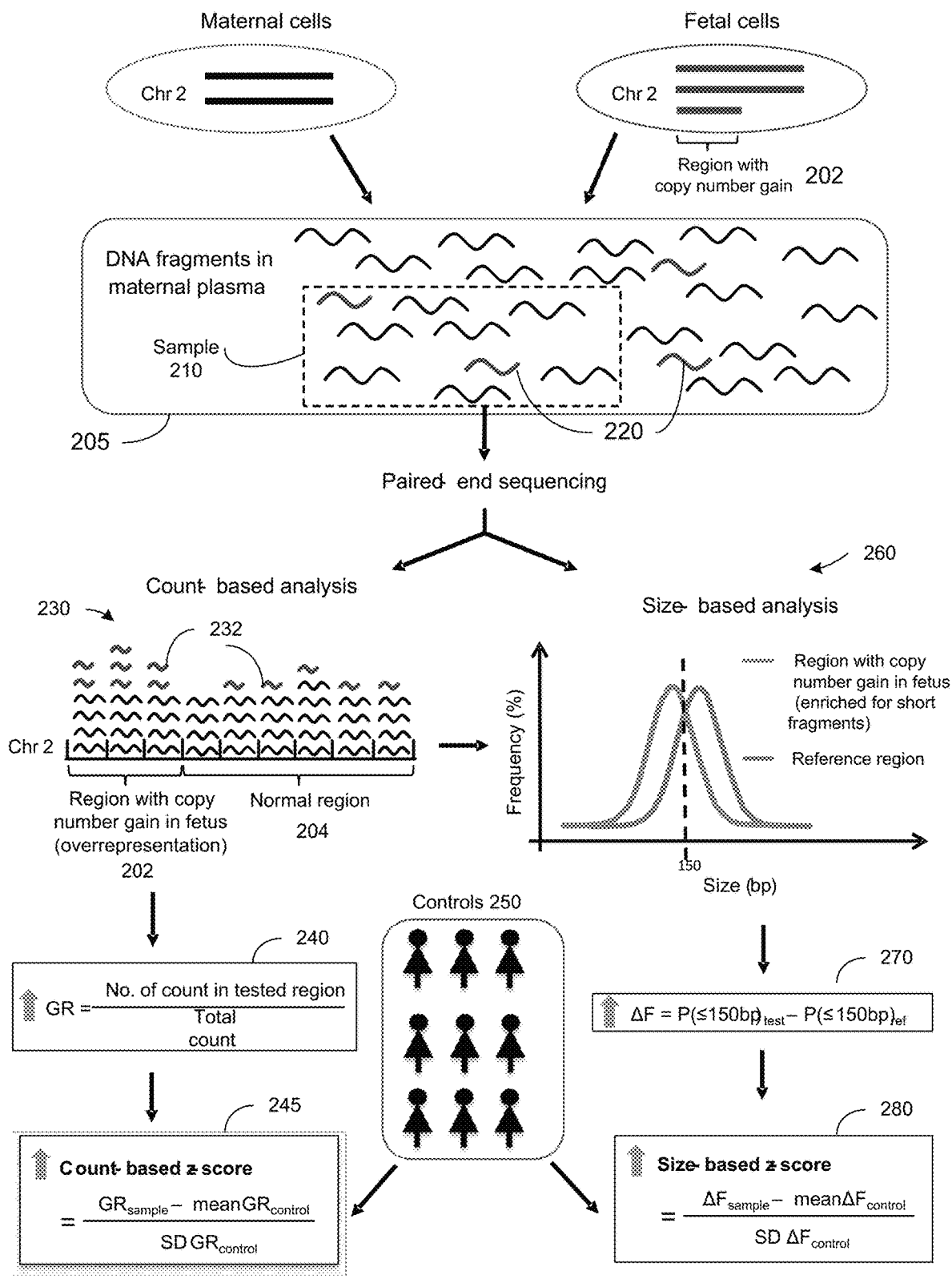
FIG. 2 shows an example process flow of a combined count- and size-based analysis for a case with a copy number gain in a region on chromosome 2 in the fetus according to embodiments of the present invention.

The term "biological sample" as used herein refers to any sample that is taken from a subject (e.g., a human, such as a pregnant woman) and contains one or more nucleic acid molecule(s) of interest. Examples include plasma, saliva, pleural fluid, sweat, ascitic fluid, bile, urine, serum, pancreatic juice, stool and cervical smear samples The term "nucleic acid" or "polynucleotide" refers to a deoxyribonucleic acid (DNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer M A et al., *Nucleic Acid Res* 1991; 19:5081; Ohtsuka E et al., *J Biol Chem* 1985; 260: 2605-2608; and Rossolini G M et al., *Mol Cell Probes* 1994; 8:91-98).

The term "sequence read" refers to a sequence obtained from all or part of a nucleic acid molecule, e.g., a DNA fragment. In one embodiment, just one end of the fragment is sequenced, e.g., about 30 bases. The sequenced read can then be aligned to a reference genome. Alternatively, both ends of the fragment can be sequenced to generate two sequenced reads, which can provide greater accuracy in the alignment and also provide a length of the fragment. In yet another embodiment, a linear DNA fragment can be circularized, e.g., by ligation, and the part spanning the ligation site can be sequenced.

The term fractional fetal DNA concentration is used interchangeably with the terms fetal DNA proportion and fetal DNA fraction, and refers to the proportion of DNA molecules that are present in a maternal plasma or serum sample that is derived from the fetus (Lo Y M D et al. *Am J Hum Genet* 1998; 62:768-775; Lun F M F et al. *Clin Chem* 2008; 54:1664-1672).

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "classification" as used herein refers to any number(s) or other characters(s) (including words) that are associated with a particular property of a sample. For example, a "+" symbol could signify that a sample is classified as having deletions or amplifications (e.g., duplications). The term "cutoff" and "threshold" refer a predetermined number used in an operation. For example, a cutoff size can refer to a size above which fragments are excluded. A threshold value may be a value above or below which a particular classification applies. Either of these terms can be used in either of these contexts.

A "subchromosomal region" is a region that is smaller than a chromosome. Examples of subchromosomal regions are those that are 100 kb, 200 kb, 500 kb, 1 Mb, 2 Mb, 5 Mb, or 10 Mb in sizes. Another example of a subchromosomal region is one that corresponds to one or more bands, or subbands, or one of the arms of a chromosome. Bands or subbands are features observed in cytogenetic analysis. A subchromosomal region may be referred to by its genomic coordinates in relation to a reference human genome sequence.

DETAILED DESCRIPTION

Maternal plasma DNA-based noninvasive prenatal testing has been expanded to include the detection of certain subchromosomal copy number aberrations (CNAs), also called copy number aberrations (CNAs). However, false-positive results are prevalent, particularly as more subchromosomal regions are analyzed. Despite having a high detection rate and a low false-positive rate, noninvasive prenatal testing (NIPT) for fetal subchromosomal aneuploidies using cell-free DNA in maternal plasma is currently not widely used as a screening test due to an insufficiently high positive predictive value.

The description below demonstrates that a size-based analysis can be used as an independent method to validate the CNAs detected by a count-based analysis. In addition, it is showed that a combination of size-based and count-based analyses can determine whether a fetus has inherited a CNA from its mother who herself is a carrier of the CNA. Embodiments using a combination of size-based and count-based analyses can differentiate the origin, i.e., fetal, maternal or both of the aberrations detected by analyzing the maternal biological sample, e.g., using sequencing and analysis of the sequencing results. This strategy improves the specificity of current tests. Results show that embodiments provide an improvement by being able to identify the origins of the CNA, which was not possible using only the count-based techniques or size-based techniques separately.

I. INTRODUCTION

Cell-free DNA in maternal plasma comprises a mixture of fetal and maternal DNA. The use of massively parallel sequencing (MPS) of cell-free DNA in maternal plasma for the noninvasive prenatal testing (NIPT) of fetal chromosomal aneuploidies has become widely adopted in prenatal care (1,2). These methods are based on the counting of DNA fragments in maternal plasma that map to different regions of the genome and hence is referred to as the "counting approach" (3). Recent studies have demonstrated that this approach can detect fetal subchromosomal abnormalities with the use of higher sequencing depth and appropriate bioinformatics analyses (4-8). In fact, a number of companies are beginning to offer NIPT for a number of clinically important and relatively common subchromosomal abnormalities, such as DiGeorge syndrome, Cri-du-chat syndrome, Prader-Willi/Angelman syndrome and the 1p36 deletion syndrome (9).

The counting approach enumerates both fetal and maternal DNA molecules in a maternal sample. It compares the relative representation of a particular genomic region in the plasma of a pregnant woman in relation to the corresponding values in a group of healthy pregnant women carrying normal fetuses. Hence, an abnormal result from the count-based approach could result from more than one clinical scenario, namely the presence of a copy number aberration (CNA) in (i) the fetus, (ii) the mother or (iii) both (8,10). As used herein, the mother can refer to the biological mother or a surrogate. The term pregnant female subject also refers to both.

Thus, if the mother carries a CNA, one could not discern if the fetus has inherited the aberration. Indeed, the presence of maternal copy number variants is one of the reported causes confounding NIPT results (11). Snyder et al. demonstrated in two cases that discordant NIPT results might be attributable to the presence of maternal copy number variants (11). In a recent study, Yin et al. reported that maternal copy number variants were present in 35 out of the 55 (63.7%) samples with false-positive NIPT results in their cohort of 1,456 samples (12). Based on this finding, Yin et al. recommend a follow-up test of the maternal DNA to exclude maternal copy number variants in cases with positive NIPT results for fetal subchromosomal aberrations. Accordingly, the presence of maternal copy number variants causes inaccuracies in the detection of fetal subchromosomal CNAs using a mixture of fetal and maternal DNA.

Recently, a group that includes the inventors of the instant disclosure developed an approach that takes advantage of the size difference between fetal and maternal DNA molecules in maternal plasma for the detection of fetal aneuploidies (13). DNA molecules (also called fragments) derived from the fetus have a shorter size distribution compared with those derived from the mother (14,15). Hence, the presence of an extra fetal chromosome in fetal trisomy would shorten the size distribution of DNA in maternal plasma derived from that chromosome. This size-based approach detects an increased proportion of short fragments from the aneuploid chromosome in the plasma. This approach has allowed the detection of multiple types of fetal whole-chromosome aneuploidies, including trisomies 21, 18, 13 and monosomy X, with high accuracy (13). An independent use of this size-based approach also suffers inaccuracies in the detection of fetal subchromosomal CNAs using a mixture of a fetal and maternal DNA when maternal copy number variants exist.

This disclosure shows that a combination of size-based and count-based analyses is shown to be able to differentiate the origin, i.e., fetal, maternal or both, of the aberrations detected by maternal plasma DNA sequencing. If both the fetus and mother have CNAs in a particular subchromosomal region, there would be no net difference in the size distribution of that region when compared with another subchromosomal region without any CNAs. On the other hand, if there is a relative overrepresentation of fetal DNA when compared with maternal DNA in a particular subchromosomal region, such as when (i) the fetus has a microduplication while the mother is normal; or (ii) the mother has a microdeletion while the fetus is normal, then there would be shortening in the overall size distribution. Conversely, if there is an underrepresentation of fetal DNA when compared with maternal DNA in a particular subchromosomal region, such as when (i) the fetus has a microdeletion while the mother is normal; or (ii) the mother has a microduplication while the fetus is normal, then there would be lengthening in the overall size distribution. In this manner, the size-based approach when combined with the count-based approach can be used to determine the origin of a subchromosomal CNA.

II. INDEPENDENT ANALYSES

To identify subchromosomal CNAs, the entire genome can be divided into subchromosomal regions (also called bins). In some embodiments, bins can be smaller than a region, where a subchromosomal region with a CNA can include multiple bins. Consecutive bins with an aberration can define a region having a CNA. In other embodiments, a region can correspond to one bin. As explained in more detail later, bins can be merged to identify a region (segment) having a CNA.

These bins may have sizes on the order of 100 kb, 200 kb, 500 kb, 1 Mb, 2 Mb, 5 Mb, or 10 Mb, for example. Subchromosomal regions can also include bands, sub-bands, and arms. In one implementation, 2,687 1-Mb bins may be used. Certain parts of the genome may be excluded, e.g., repeat regions. These subchromosomal regions can be analyzed using a count-based method and a size-based method to determine whether the region includes an amplification or a deletion. The aberration may not correspond to the entire region, but a region can be tested to identify whether an aberration occurs somewhere in the region.

As part of the analyses, cell-free DNA fragments in the maternal sample are analyzed to determine locations of the DNA fragments in the genome, e.g., with respect to a reference genome. For example, the cell-free DNA fragments can be sequenced to obtain sequence reads, and the sequence reads can be mapped (aligned) to the reference genome. If the organism was a human, then the reference genome would be a reference human genome, potentially from a particular subpopulation. As another example, the cell-free DNA fragments can be analyzed with different probes (e.g., following PCR or other amplification), where each probe corresponds to a different genomic location. In some embodiments, the analysis of the cell-free DNA fragments can be performed by receiving sequence reads or other experimental data corresponding to the cell-free DNA fragments, and then analyzing the experimental data using a computer system.

A. Count-Based Analysis

To perform the count-based analysis, embodiments can count a number of DNA fragments from the maternal sample that are located in each region. The number of DNA fragments in a region can be compared to one or more count thresholds to determine whether the region exhibits a CNA. The count threshold(s) can be determined based on corresponding counts in regions of healthy controls so as to discriminate between CNAs and regions without a CNA. If the number is above a high threshold, then an amplification be identified. If the number is below a low threshold, then a deletion can be identified. One skilled in the art will know how to determine such thresholds.

The number of DNA fragments is normalized such that comparisons can be made across different subjects, where different amount of DNA fragments may be analyzed. The normalization can be performed in many ways, for example by dividing the respective number for a region by a sum of respective numbers for one or more other regions (potentially the entire genome). This comparison to respective numbers for one or more other regions can also be done by always analyzing a same number of DNA fragments from sample to sample, which makes the sum always the same. Therefore, the count number for a region can be used directly, e.g., as the sum can be effectively included in the threshold. Thus, the ratio of numbers is still performed in such an embodiment. Accordingly, embodiment can compute a count parameter from a first number for a first region and a second number for a second region.

A normalized number of DNA fragments in a region can also be referred to as a genomic representation (GR). The normalization is performed by a ratio to a second number of DNA fragments for a different region. For example, the GR for a region can be a number of DNA fragments located in the region divided by all of the DNA fragments used in the analysis. A GR of a region can correspond any amount, e.g., a number of DNA fragments, a number of bases to which a DNA fragment overlapped, or other measure of DNA fragments in a region.

In some embodiments, the count parameter can correspond to a score, e.g., in the following manner. The mean values and standard deviations (SDs) of the genomic representation (GR) of the tested region of the controls can be determined. A count-based z-score can be calculated for the tested region of each sample using the following equation (7):

$$\text{Count-based } z\text{-score} = \frac{GR_{sample} - \text{mean } GR_{control}}{SD \ GR_{control}}$$

In examples herein, count-based z-scores of >3 and <−3 were used as the count thresholds for indicating a copy number gain and a copy number loss, respectively. In such an example the z-score can correspond to a count parameter that is compared to 3 or −3. Other count thresholds can be used, e.g., values other than 3. In other examples, GRsample is a count parameter and the other terms can be moved to the left side of the equation to be used as part of the count threshold. Further details of a count-based approach can be found in U.S. Patent Publication 2009/0029377.

B. Size-Based Analysis

As mentioned above, fetal DNA fragments are smaller than maternal DNA fragments. This difference in size can be used to detect a CNA in a fetus. If a fetus has an amplification in a first region, then the average size of the DNA fragments for that region will be lower than a second region that does not have an amplification; the extra, smaller fetal DNA in the first region will decrease the average size. Similarly, for a deletion, the fewer fetal fragments for a region will cause the average size be larger than for normal regions. Examples of size include length or mass.

Other statistical values can be used, e.g., a cumulative frequency for a given size or various ratios of amount of DNA fragments of different sizes. A cumulative frequency can correspond to a proportion of DNA fragments that are of a given size or smaller. The statistical values provide information about the distribution of the sizes of DNA fragments for comparison against one or more size thresholds for healthy control subjects. As with the count thresholds, one skilled in the art will know how to determine such thresholds.

Accordingly, to perform the size-based analysis, embodiments can calculate a first statistical value of sizes of nucleic acid molecules located in the first subchromosomal region, and calculate a reference statistical value of sizes of nucleic acid molecules located in the reference region. A separation value (e.g. a difference or ratio) can be determined between the first statistical value and the reference statistical value. The separation value can be determined from other values as well. For example, the reference value can be determined from statistical values of multiple regions. The separation value can be compared to a size threshold to obtain a size classification (e.g., whether the DNA fragments are shorter, longer, or the same as a normal region).

Some embodiments can calculate a parameter (separation value) for each of the tested regions, which is defined as the difference in the proportion of short DNA fragments between the tested and the reference regions using the following equation (13):

$$\Delta F = P(\leq 150 \text{ bp})_{test} - P(\leq 150 \text{ bp})_{ref}$$

where $P(\leq 150 \text{ bp})_{test}$ denotes the proportion of sequenced fragments originating from the $_{test}$ tested region with sizes ≤150 bp, and $P(\leq 150 \text{ bp})_{ref}$ denotes the proportion of sequenced fragments originating from the reference region with sizes ≤150 bp. In other embodiments, other size thresholds can be used, for example but not limited to 100 bp, 110 bp, 120 bp, 130 bp, 140 bp, 160 bp and 166 bp. In other embodiments, the size thresholds can be expressed in bases, or nucleotides, or other units. In some implementations, the reference region can be defined as all the subchromosomal regions excluding the tested regions. In other implementations, the reference region can be just a portion of the subchromosomal regions excluding the tested regions.

The same groups of controls used in the count-based analysis can be used in the size-based analysis. A size-based z-score of the tested region can be calculated using the mean and SD values of ΔF of the controls (13).

$$\text{Size-based } z\text{-score} = \frac{\Delta F_{sample} - \text{mean } \Delta F_{control}}{SD \ \Delta F_{control}}$$

In some embodiments, a size-based z-score of >3 indicates an increased proportion of short fragments for the tested region, while a size-based z-score of <−3 indicates a reduced proportion of short fragments for the tested region. Other size thresholds can be used. Further details of a size-based approach can be found in U.S. Pat. No. 8,620,593.

To determine a size of a DNA fragment, at least some embodiments can work with any single molecule analysis platform in which the chromosomal origin and the length of the molecule can be analyzed, e.g. electrophoresis, optical methods (e.g. optical mapping and its variants, en.wikipedia.org/wiki/Optical_mapping #cite_note-Nanocoding-3, and Jo et al. Proc Natl Acad Sci USA 2007; 104:2673-2678), fluorescence-based method, probe-based methods, digital PCR (microfluidics-based, or emulsion-based, e.g. BEAMing (Dressman et al. Proc Natl Acad Sci USA 2003; 100: 8817-8822), RainDance (raindancetech.com/technology/pcr-genomics-research.asp)), rolling circle amplification, mass spectrometry, melting analysis (or melting curve analysis), molecular sieving, etc. As an example for mass spectrometry, a longer molecule would have a larger mass (an example of a size value).

In one example, DNA molecules can be randomly sequenced using a paired-end sequencing protocol. The two reads at both ends can be mapped (aligned) to a reference genome, which may be repeat-masked. The size of the DNA molecule can be determined from the distance between the genomic positions to which the two reads mapped.

III. COMBINED COUNT-BASED AND SIZE APPROACH

The count-based approach compares the relative representation of a particular genomic region in relation to a group of healthy pregnant women carrying normal fetuses. Hence, an abnormal result from the count-based approach would inform that either the fetus or the mother, or both have a copy number aberration. On the other hand, the size-based approach is based on the difference in the size distribution of DNA molecules in the maternal sample, depending on the origin of the DNA molecules. Hence, DNA molecules derived from the fetus would have a shorter size distribution compared with those derived from the mother. Thus, if both the fetus and mother have copy number aberrations in a particular subchromosomal region, then there would be no net difference in the size distribution in that region when compared with another subchromosomal region not having the copy number aberrations.

On the other hand, if there is an overrepresentation of fetal DNA when compared with maternal DNA in a particular subchromosomal region, such as when (i) the fetus has a microduplication (or microamplification of a larger extent) while the mother is normal; or (ii) the mother has a microdeletion while the fetus is normal, then there would be shortening in the size distribution. Conversely, if there is an underrepresentation of fetal DNA when compared with maternal DNA in a particular subchromosomal region, such as when (i) the fetus has a microdeletion while the mother is normal; or (ii) the mother has a microduplication while the fetus is normal, then there would be lengthening in the size distribution.

FIG. 1 shows a table 100 of six scenarios for combinations of count-based and size-based outcomes according to embodiments of the present invention. In some embodiments, the size-based classification of normal corresponds to when a statistical value is approximately equal to an expected value, e.g., a reference control. Column 110 shows various statuses of the mother as duplication (or amplifications of a larger extent), deletion, or normal. Column 120 shows various statuses of the fetus as duplication (or amplifications of a larger extent), deletion, or normal. Column 130 shows the count-based classifications of over-represented (corresponds to positive count-based z-score in example above) and under-represented (corresponds to negative count-based z-score in example above). Column 140 shows the size-based classifications of normal (same sizes in the two regions), shorter (corresponds to positive size-based z-score in example above) and longer (corresponds to negative size-based z-score in example above).

Looking at table 100, cases with CNAs derived solely from the fetus would have a size-based z-score in the same direction as the count-based z-scores. For example, a positive value for the count-based z-score indicates an over-representation of DNA fragments for that region, and a positive value for the size-based z-score indicates that the DNA fragments are shorter for that region, thereby suggesting an amplification (e.g., a duplication) solely for the fetus. Conversely, negative values for both the count-based z-score and the size-based z-score indicate under-representation and longer DNA fragments respectively for that region, thereby suggesting a deletion solely for the fetus.

For cases in which the mother carries the CNA, size-based analysis would be useful to determine whether the fetus has inherited the aberration from the mother. Cases in which the fetus has inherited the aberration from the mother would have a size-based z-score within the normal range because there is no change in the relative proportion of fetal and maternal DNA for the affected region compared with other genomic regions. For example, an over-representation classification for the count-based analysis and a normal classification for the size-based analysis shows that the fetus inherited the amplification. And, an under-representation classification for the count-based analysis and a normal classification for the size-based analysis shows that the fetus inherited the deletion.

On the other hand, cases with CNAs only present in the mother would have a size-based z-score in the opposite direction to the count-based z-scores. Thus, a positive count-based z-score (over-represented classification) and a negative size-based z-score (longer classification) indicates a maternal duplication and a normal status for the fetus. Conversely, a negative count-based z-score (under-represented classification) and a positive size-based z-score (shorter classification) indicates a maternal deletion and a normal status for the fetus.

A. Performing Combined Analysis

FIG. 2 shows an example process flow of a combined count- and size-based analysis for a case with a copy number gain in a region on chromosome 2 in the fetus according to embodiments of the present invention. Maternal cells are shown as normal for chromosome 2, and fetal cells are shown as having a duplication for a region 202.

Cell-free DNA fragments are shown being present in maternal plasma 205. DNA molecules derived from the fetus (thick red fragments 220) have a shorter size distribution than those derived from the mother (black fragments). A sample 210 is taken of the maternal plasma. As shown, paired-end sequencing is performed to obtain sequence reads. Paired-end sequencing (which includes sequencing an entire DNA fragment) can be used to determine a size of a DNA fragment as well as its location, e.g., when the sequence read(s) are mapped to a reference genome.

In the count-based analysis, at block 230, DNA fragments aligning to respective bins 232 of chromosome 2 are counted. The bins of region 202 are identified as having a higher amount than the bins of a normal region 204. In this example, the bins used for counting are smaller than the region used for analyzing a z-score. In other examples, separate determinations can be made for each bin (thus, a bin would be the same size as a region). In some embodiments, multiple consecutive bins can be required to show a same aberration, e.g., as U.S. Patent Publication 2014/0195164, which is incorporated by reference in its entirety. Thus, even though one bin in normal region 204 has as high of a count as two bins in region 202, the bin is still included in normal region 204.

At block 240, the genomic representation (GR) of region 202 is determined as the number of counts of sequence reads in region 202 divided by a total count of sequence reads. In other embodiments, the denominator could be the count of sequence reads for only some bins.

At block 245, a count-based z-score is determined. Values of z-scores from controls 250 can be used, e.g., to determine a mean and a standard deviation (SD) for the controls. The control values can be for the same test region in the control subjects or for other regions of a similar size. The count-based z-score is shown with an upward arrow indicating a positive score that is greater than a count threshold.

At block 260, the size-based analysis can receive an identification of region 202 showing an over-representation. The size-based analysis shows size distributions for region 202 and for a reference region. As shown, the size distribution for region 202 is smaller than the size distribution for the reference region. The determination of this relationship between the size distributions can be determined in the following blocks using statistical values of the size distributions.

At block 270, a separation value $\Delta F$ is determined from $P(\leq 150 \text{ bp})_{test}$ and $P(\leq 150 \text{ bp})_{ref}$. Other statistical values can be used for other examples. The separation value is shown as positive since region 202 has a higher proportion of DNA fragments of 150 bases or less.

At block 280, a size-based z-score is determined. Values of z-scores from controls 250 can be used, e.g., to determine a mean and a standard deviation (SD) for the controls. The control values can be for the same test region in the control subjects or for other regions of a similar size. The size-based z-score is shown with an upward arrow indicating a positive score that is greater than a size threshold, which corresponds to the DNA fragments of region 202 being smaller than the reference region.

Per table 100 of FIG. 1, the count-based classification of over-represented and the size-based classification of shorter indicate that only the fetus has an amplification for region 202. In this manner, embodiments can be used for determining whether the fetus, the mother, or both have the identified aberration.

B. Method

Figure 3:
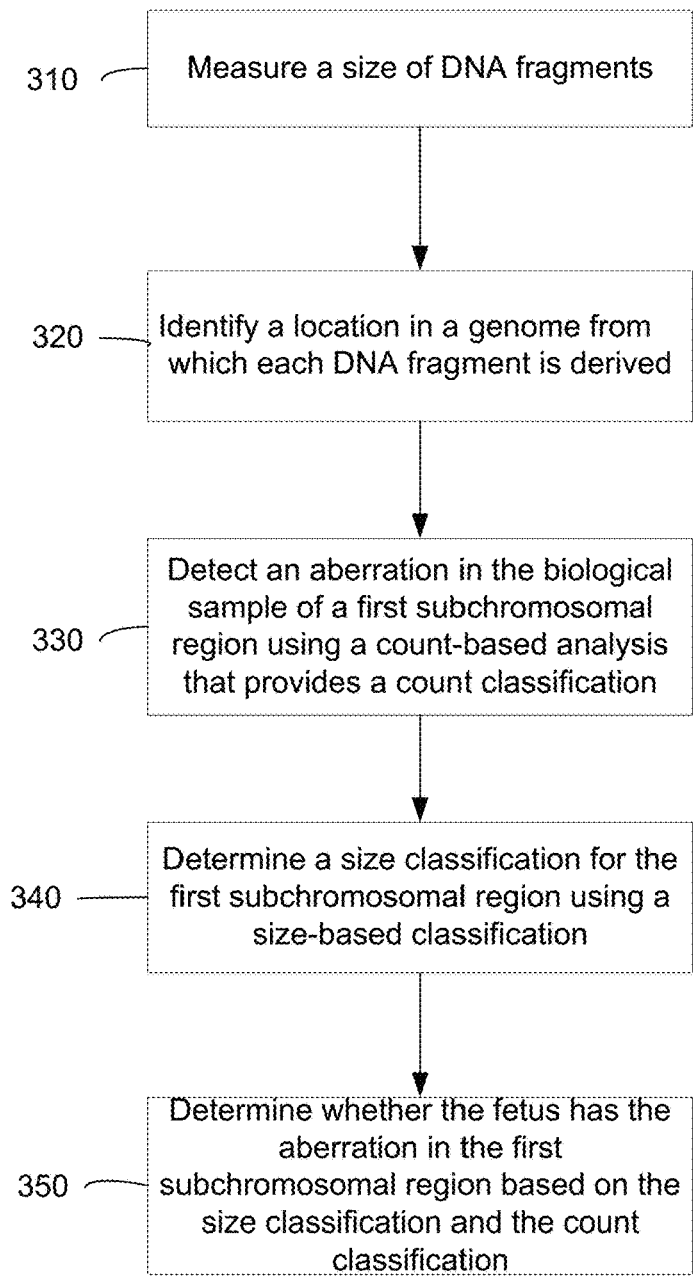
FIG. 3 is a flowchart of a method 300 of identifying a subchromosomal aberration in a fetal genome of a fetus by analyzing a biological sample from a female subject pregnant with the fetus according to embodiments of the present invention.

FIG. 3 is a flowchart of a method 300 of identifying a subchromosomal aberration in a fetal genome of a fetus by analyzing a biological sample from a female subject pregnant with the fetus according to embodiments of the present invention. The biological sample includes cell-free DNA molecules from the female subject and the fetus. Method 300 may be performed entirely or partially with a computer system.

At block 310, a size of at least some of the DNA molecules in the biological sample is measured. The DNA molecules are also referred to as fragments, as they are a fragment of the entire genome, as well as a fragment of a chromosome. The size may be measured via any suitable method, for example, methods described above.

At block 320, a location is identified in a reference genome from which each of the nucleic acid molecules is derived. The location can be any part of a genome, which is human for the examples provided, but could be for other genomes. For example, the location can be a part of a chromosome as may be defined by genomic coordinates (e.g. a specific coordinate or range of coordinates).

In one embodiment, the identification can be performed by sequencing and comparing the sequence information with the reference human genome sequence. In another embodiment, this identification can be performed by hybridization to a panel of probes with known chromosomal origin. The probes could be labeled with one or more fluorescence labels, in either a microarray format or in solution. In yet another embodiment, the nucleic acid molecules could be captured by a panel of probes, either in solution or on a solid surface, and then the captured (or the remaining non-captured) nucleic acid molecules are sequenced.

At block 330, an aberration is detected in the biological sample of a first subchromosomal region using a count-based analysis, e.g., as described in section II.A. For example, the reference genome can be divided into bins, and the DNA fragments mapping to each bin can be counted. Based on the counts, it can be determined whether a region is over-represented or under-represented as part of detecting an aberration. If neither an over-representation or an under-representation is determined, then the region can be identified as normal.

In some embodiments, a first amount of DNA molecules located in the first subchromosomal region can be determined using the location determined in block 320. As examples, the first amount can correspond to a number of DNA molecules located entirely within the first subchromosomal region, partially within the first subchromosomal region, and a number of genomic positions that DNA molecules overlap with the first subchromosomal region.

A second amount of DNA molecules located in a second region can be determined. In various examples, the second region can be the entire genome, just one subchromosomal region, a chromosome (which may include the first subchromosomal region), and disjoint subchromosomal regions, e.g., all other regions not being tested. A count parameter can be computed from the first amount and the second amount. The count parameter can be compared to one or more count threshold to determine a count classification of a type of aberration existing in the biological sample for the first subchromosomal region.

Examples of types of aberrations are a deletion, a duplication, and higher order amplifications. Each of the aberrations can correspond to a different count threshold. For example, a deletion can be determined when the count parameter is less than a low threshold, which would be below that of a region for which no aberration exists. An amplification can be determined when the count parameter is greater than a high threshold, which would be higher than that of a region for which no aberration exists. As mentioned above, the second amount can be included in a count threshold, which just changes the value of the threshold, and thus is the same as determining a count parameter from the first amount and the second amount.

At block 340, a size classification is determined for the first subchromosomal region using a size-based analysis. The size classification can indicate whether a size distribution of DNA molecules located in the first subchromosomal region is shorter, longer, or the same as that of the reference region. As fetal DNA molecules are smaller, the analysis of the size distribution can indicate whether there are more (shorter sizes than reference) or less (larger sizes than reference) fetal DNA proportion than for the reference region, thereby indicating whether there is an overabundance, same, or underabundance of fetal DNA relative to the reference region. In various examples, the reference region can be the entire genome, just one subchromosomal region, a chromosome (which may include the first subchromosomal region), and disjoint subchromosomal regions, e.g., all other regions not being tested. As explained above for FIG. 1, the size classification can be used to discriminate between different possibilities of aberration among the fetus and the mother.

In some embodiments, a first statistical value of sizes of DNA molecules located in the first subchromosomal region can be calculated. Examples of statistical sizes are average size, size at a peak of a size distribution, a mode of the size distribution, a cumulative frequency at a given size, and the like. A reference statistical value of sizes of DNA molecules located in a reference region can be determined for comparison to the first statistical value. A separation value between the first statistical value and the reference statistical value can be determined. The separation value can provide a measure of a relative proportion of fetal DNA molecules in the first subchromosomal region relative to the reference region. The separation value can be compared to one or more size thresholds to obtain the size classification.

At block 350, it is determined whether the fetus has the aberration in the first subchromosomal region based on the size classification and the count classification. The determination can be made using FIG. 1, where the size classification can be used to discriminate between three possibilities each for the count classifications of over-represented and under-represented. For example, the over-represented classification can occur when the fetus, the mother, or both have an amplification.

If only the fetus has the amplification, then there will be a greater proportion of fetal DNA molecules in the first subchromosomal region than in the reference region, and the size distribution will be shorter for the first subchromosomal region. If only the mother has the amplification, then there will be a smaller proportion of fetal DNA molecules in the first subchromosomal region than in the reference region, and the sizes will be longer for the first subchromosomal region. If both the mother and the fetus have the amplification, then the proportion of fetal DNA to maternal DNA will be the same as both have elevated amounts, and thus the size distributions will be the same, resulting in a normal classification.

Many apparent aberrations present in the sample would be non-pathogenic copy number variations (CNVs), which are normally present in the human population. Therefore, the aberrations detected in the sample can be further scored or ranked by comparing to a variety of databases. Such databases have information as to whether a CNV is present in a region of interest in a particular human population, the type of CNVs (deletion or duplication; gain or loss), frequency of CNVs, and whether a pathogenic aberration is reported in a region of interest. For example, the short list of aberrations identified from plasma DNA can be compared with the CNVs identified in 1000 genomes (1000genomes.org/), CNVs curated in database of variants (DGV, dgv.tcag.ca/dgv/app/home), and/or a list of expert-curated microdeletion and microduplication syndromes involved in developmental disorders recorded in DECIPHER database (decipher.sanger.ac.uk/).

In one embodiment, an aberration identified in the sample overlapping with known pathogenic aberrations would be assigned a higher score while the aberration identified in the sample overlapping with a known non-pathogenic CNVs would be assigned a lower score. The scores for each aberrant region can be combined to provide an overall pathogenic score.

IV. ABERRATION-CONTAINING FRACTION

The magnitude of the count-based z-score of the abnormal region correlates with the proportion of plasma DNA harboring the aberration (17). For example, if only the fetus has the aberration, then the proportion of plasma DNA harboring the aberration would correlate to the proportion of fetal DNA in the plasma sample. The proportion of plasma DNA harboring the aberration can be used as an additional screen to identify cases where the mother has the aberration.

Aberration-containing fraction in the plasma ($F_{CNA}$, also referred to as AcF) refers to the proportion of plasma DNA derived from cells with a CNA. Theoretically, if only the fetus carries the aberration, only those fetal-derived plasma DNA molecules would contain the aberration; and $F_{CNA}$ would be equal to the fetal DNA fraction in plasma. Analogously, if only the mother carries the aberration, only those maternally-derived plasma DNA molecules would contain the aberration; and $F_{CNA}$ would be equal to the maternal DNA fraction in plasma. On the other hand, if both the mother and the fetus carry an aberration that is not mosaic in nature (i.e. only some of the cells carry the aberration), all plasma DNA molecules would be derived from cells containing the aberration; and $F_{CNA}$ would be 100%.

In some embodiments, to calculate $F_{CNA}$, the entire genome can be divided into 2,687 1-Mb bins, also called bins. A count-based z-score can be calculated for each bin as described above. The 1-Mb bin with the highest z-score in the region showing the CNA can be used for the calculation of $F_{CNA}$. If the region had only one bin, then that bin would be used. The $F_{CNA}$ can be calculated as follows (7):

$$F_{CNA} = \left| \frac{GR_{sample} - \text{mean } GR_{control}}{\text{mean } GR_{control}} \right| \times 100\% \times 2$$

$GR_{sample}$ is the genomic representation of the 1-Mb bin with the highest z-score in the affected region for the test case, and mean $GR_{control}$ is the mean of the genomic representation of that bin in the controls. The $F_{CNA}$ is another example of a count parameter, which can be compared to a count threshold to determine whether or not an aberration exists. But, the $F_{CNA}$ can also be used in other ways.

The $F_{CNA}$ can be calculated for each region showing a CNA. The $F_{CNA}$ can be used to determine if the aberration is present in the mother. Given that over 99% of maternal plasma samples would have a fetal DNA fraction of less than 50% (17,18), cases with $F_{CNA}$>50% would suggest that the mother carries the copy number aberration, and thus it is unlikely to be a fetal-only aberration. For cases with $F_{CNA}$<50%, the CNA is potentially present in the fetus. In one embodiment, if $F_{CNA}$ is less than 50% (or other cutoff value), then the aberration is determined to be fetal or mosaic in the mother.

FIG. 4 shows a table 400 of the six scenarios for combinations of count-based and size-based outcomes along with $F_{CNA}$ values according to embodiments of the present invention. Table 400 is similar to table 100 of FIG. 1. Column 410 shows various statuses of the mother as normal, copy number gain (amplification), and copy number loss (deletion). Column 420 shows various statuses of the fetus.

Column 430 shows the count-based classifications. A green upward pointing arrow indicates a positive count-based z-score greater than a high count threshold (e.g., >3). A red downward pointing arrow indicates a negative count-based z-score less than a low count threshold (e.g., <−3). Double arrows indicate a large magnitude count-based z-score. A large magnitude count-based z-score can correspond to a $F_{CNA}$ of a certain threshold of, for example but not limited to, >40%, >45%, >50%, >55% and >60%. Different cutoff values can be used to define a "large magnitude z-score", for example but not limited to >10, >15, >20, >25, >30, >35, >40, >45, >50, >55, >60 for positive z-scores and <−10, <−15, <−20, <−25, <−30, <−35, <−40, <−45, <−50, <−55 for negative z-scores.

Column 440 shows the size-based classifications. A green upward pointing arrow indicates a positive size-based z-score greater than a high size threshold (e.g., >3). A red downward pointing arrow indicates a negative count-based z-score less than a low count threshold (e.g., <−3).

Column 435 shows whether $F_{CNA}$ is greater than or less than 50% for each of the combinations. As shown, when the $F_{CNA}$ is greater than 50%, the mother would have the aberration. Thus, the $F_{CNA}$ can be calculated to determine if the aberration is present in the mother. $F_{CNA}$>50% suggests that the mother carries the copy number aberration. In other embodiments, other thresholds for $F_{CNA}$ can be used, for example but not limited to >40%, >45%, >55% and >60%.

Accordingly, a first bin count parameter (e.g., $GR_{sample}$) for a first bin of the first subchromosomal region can be determined. The first subchromosomal region can include one or more bins. The first bin count parameter can be determined from an amount of DNA molecules located in the first bin normalized by an amount of DNA molecules located in another region, which can be the same region or a different region than that used for normalization of the first subchromosomal region. A mean of control bin count parameters (e.g., mean $GR_{control}$) for the first bin can be computed using control samples. A first score (e.g., $F_{CNA}$) can be computed for the first bin by subtracting the mean of the control bin count parameters to obtain a result and dividing the result by the mean of the control bin count parameters, e.g., as shown above. Whether the first score (e.g., absolute value) is greater than a cutoff value (50% for the example above) can be used to identify whether the female subject has the aberration for the first subchromosomal region. Other cutoff values can be used depending on the definition of the first score, e.g., whether the factors of 2 and 100% are used.

V. RESULTS

The results below confirm the ability of embodiments to correctly identify whether a detected subchromosomal aberration is from the fetus, the mother, or both. Such results show an improvement over existing techniques that would misclassify all subchromosomal aberrations as being from the fetus, which leads to false positives.

A. First Set of Results

A paired-end sequencing data of six maternal plasma DNA samples with known fetal microdeletions and microduplications from a previous study were analyzed with the size profiling method. Among the six test cases, there were five cases of fetal-derived subchromosomal deletions or duplications involving chromosomes 3q, 4q and 22q, and one case of maternally-inherited microduplication on 22q. The size of each sequenced DNA fragment was determined from the start and end coordinates of the paired-end reads.

For each test case, the target region was defined as the copy number aberration-containing region identified by count-based analysis. The reference region (second region of method 300) encompasses all the unaffected genomic regions on the non-aberration-containing autosomes. The same group of eight singleton pregnant cases with normal fetal karyotypes that was used in a previous study for count-based analysis was applied in the size analysis as the reference controls (7). A size-based z-score for the target region for each test sample was then calculated deletion.

FIG. 5 is a table 500 showing count-based scores and size-base scores for six maternal plasma DNA samples for illustrating accuracy of embodiment of the present invention. The count-based z-scores show aberrations as existing. The range of count-based scores corresponds to 1-Mb bins of the regions.

Using table 400 of FIG. 4, cases with copy number aberrations derived solely from the fetus would have a size-based z-score that is in the same direction as the count-based z-scores, namely a positive number would suggest an amplification while a negative number would suggest a deletion. Using a z-score cutoff of 3 SDs from the mean, all the copy number aberrations detected by the count-based method in cases 01-04 and 06 were independently confirmed to be exclusively derived from the fetuses (as shown in in table 500).

Case 05 is a pregnancy involving a fetus that has inherited a microduplication of 2.4 Mb on chromosome 22q from its mother. Since the mother herself carried the microduplication, there are very high count-based z-scores for the three 1-Mb bins involved (range, 39.7 to 71.7). However, this analysis by itself does not reveal whether the fetus had inherited the microduplication from the mother.

Using the size-based analysis in combination with the count-based analysis, the merged 3-Mb bin showed a size-based z-score within the normal range. This observation is consistent with the size distribution of maternal plasma DNA in the affected region remaining unchanged (as the relative contribution from the fetus and mother is not altered) when an aberration is derived from both the fetus and the mother. On the other hand, if the fetus had not inherited the microduplication from the mother, the proportion of short fragments in the affected region would be reduced, leading to a negative size-based z-score in contrast to the positive count-based z-score.

B. Second Set of Results

FIG. 6 is a table 600 showing information about six cases with CNAs derived from either the fetus or the mother, or both. Three of the cases have been included in a previous study evaluating only the count-based approach (7). The remaining three were new cases that have not been analyzed before. Singleton pregnant cases with normal fetal and maternal karyotypes were used as controls. Since the three new cases and the three cases that had been included in the previous study were prepared with different library preparation kits, two different sets of controls were used in the analyses of these two groups of test cases. Each set was prepared with the same library preparation kit and sequenced with the same number of lanes as the corresponding group of test cases.

Column 610 shows the known status of whether the aberration is present or absent for the mother. Column 620 shows the known status of whether the aberration is present or absent for the fetus. To test whether embodiments could predict the known statuses, a combined count-based and size-based analyses was perform on four target regions, which include two 2-Mb regions on chromosome 4, one 4-Mb region on chromosome 12, and one 3-Mb region on chromosome 22, for each case.

Figure 7:
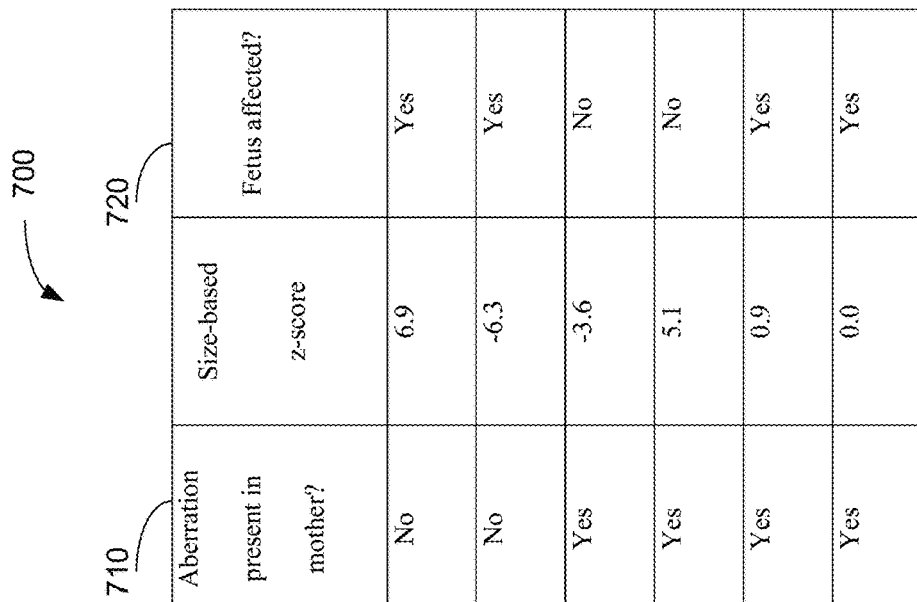
FIG. 7 shows a combined count-based and size-based analysis of maternal plasma DNA for the six cases in table 600 according to embodiments of the present invention.

FIG. 7 shows a combined count-based and size-based analysis of maternal plasma DNA for the six cases in table 600 according to embodiments of the present invention. The scores in FIG. 7 can be analyzed using table 400 of FIG. 4 to predict whether the aberrations are on the fetus, the mother, or both. Column 710 shows the predicted status of whether the aberration is present or absent for the mother. Column 720 shows the predicted status of whether the aberration is present or absent for the fetus. The predictions in columns 710 and 720 correspond to the known statuses in columns 610 and 620.

For the two cases (M10219 and HK310) in which CNAs were present only in the fetus, the size-based approach confirmed the aberrations detected by the count-based approach. For the four cases in which the mother herself carried an aberration, embodiments successfully deduced that two of the fetuses had inherited the aberrations and that the other two fetuses had not inherited the aberrations. No false positives were observed in this cohort.

For M10219, a 3-Mb microduplication on chromosome 22 was detected with a count-based z-score of 13.4. For HK310, a 3-Mb microdeletion was detected in the same region with a count-based z-score of −8.2. The $F_{CNA}$ of these two cases were 21.3% and 15.1%, respectively. Size-based z-scores of this region for M10219 and HK310 were 6.9 and −6.3, respectively, indicating that the affected region had a shorter size distribution in M10219 and a longer size distribution in HK310. In both cases, the size-based z-scores were in the same direction as the count-based z-scores, indicating that the fetus was the sole source of the aberrations detected in maternal plasma. These results were consistent with the clinical information of the two cases in FIG. 6.

For M14-13489-F1, a 2-Mb microduplication was detected on chromosome 4 with a count-based z-score of 93.8. For DNA 11-04530, a 2-Mb microdeletion was detected in another region on chromosome 4 with a count-based z-score of −61.9. The $F_{CNA}$ were 69.1 and 82.5, respectively. For the regions with abnormal count-based z-scores, the corresponding size-based z-score was −3.6 for M14-13489-F1 and 5.1 for DNA 11-04530. Hence, in both cases, the size-based z-scores were in the opposite direction to the count-based z-scores, suggesting that the aberrations would be present in the mothers only. These results were consistent with the clinical information in FIG. 6. These results show an instance where improvements are made over current techniques that assign all aberrations to the fetus. Here, such false positives are avoided.

For PW503 and M11879, a 3-Mb microduplication was detected on chromosome 22 (count-based z-score: 71.6), and a 4-Mb microduplication was detected on chromosome 12 (count-based z-score: 154.5). The $F_{CNA}$ of these two cases were 100% and 99.6%, respectively. Size-based analysis of the target regions showed size-based z-scores that were within the normal range for both cases (size-based z-scores:

0.9 for PW503 and 0.0 for M11879), indicating that both the mother and the fetus in these two cases harbored the microduplications. These results were also consistent with the clinical information in FIG. 6.

PW503 and M11879 were pregnancies involving fetuses that had inherited a microduplication of 2.4 Mb on chromosome 22q and a microduplication of 3.5 Mb, respectively, from their mothers. Since the mother herself carried the microduplication, very high count-based z-scores were determined. However, the count-based analysis by itself did not reveal whether the fetus had inherited the microduplication from the mother. Using the size-based approach, the 3-Mb and 4-Mb regions for the two cases, respectively, showed size-based z-scores within the normal range. This observation is consistent with the size distribution of maternal plasma DNA in the affected region remaining unchanged, as the relative contributions from the fetus and mother are not altered in the affected region compared with other unaffected regions when an aberration being derived from both the fetus and the mother. On the other hand, as in M14-13489-F1, when the fetus had not inherited the microduplication from the mother, the proportion of short fragments in the affected region would be reduced, leading to a negative size-based z-score in contrast to the positive count-based z-score.

FIG. 8 is a table 800 showing count-based and size-based z-scores of the tested regions with no detectable CNAs in each case according to embodiments of the present invention. No aberrations were detected in the other tested regions for each case with the combined analyses. With the count-based approach alone, an overrepresentation was detected in a 3-Mb region on chromosome 22 in M14-13489-F1 with a count-based z-score of 6.61. The $F_{CNA}$ was 14.8% and the size-based z-score was −0.82. Hence, the aberration detected by the count-based analysis was not confirmed by the size-based analysis, and this region was classified as normal which was consistent with the array CGH analysis.

Accordingly, the $F_{CNA}$ can be used to differentiate between an instance where the mother and the fetus both have the aberration and a false positive in the count-based analysis. In the above example for M14-13489-F1, the $F_{CNA}$ was 14.8%, which is well below 50%. Thus, it is unlikely that both the mother and the fetus exhibit the aberration, which would correspond to the count-based analysis being positive and the size-based analysis showing normal. In this manner, $F_{CNA}$ can be used as a further check. Thus, in some embodiments, it can be determined that no aberration exists in the first subchromosomal region when the first score is less than the cutoff value and when: the count classification indicates the amplification and the size classification indicates the aberration does not exist in the first subchromosomal region, or the count classification indicates the deletion and the size classification indicates the aberration does not exist in the first subchromosomal region.

The above data for the second set of results was sampled and processed in the following manner. Women with singleton pregnancies were recruited from the Departments of Obstetrics and Gynaecology of the Prince of Wales Hospital and Kwong Wah Hospital, Hong Kong, and the Radboud University Medical Center, The Netherlands, with written informed consent and institutional ethics committee approval. Maternal peripheral blood samples were collected and processed as previously described (16). DNA was extracted from the plasma with the QIAamp DSP DNA Blood Mini Kit (16).

Plasma DNA sequencing was performed in the following manner. We prepared DNA libraries of the new cases using a KAPA Library Preparation Kit (Kapa Biosystems) following the manufacturer's instructions. The adaptor ligated plasma DNA was enriched by a 12-cycle PCR. Each library was sequenced with two lanes of a flow cell on a HiSeq 1500 or a HiSeq 2500 sequencer (Illumina). We performed 50 cycles of paired-end sequencing. Paired-end reads were aligned and filtered as previously described (13). After alignment, the size of each sequenced DNA fragment was determined from the start and end coordinates of the paired-end reads.

For the three cases that had been included in a previous study, paired-end sequencing data of these maternal plasma DNA samples were reanalyzed as described below. The plasma DNA libraries of these cases were prepared previously with the Paired-End Sequencing Sample Preparation Kit (Illumina) and sequenced with one lane of a flow cell on a HiSeq 2000 sequencer (Illumina).

VI. MERGED SEGMENTS

As mentioned above, bins can be smaller than an aberrant region, and consecutive bins showing an aberration can be combined to identify an aberrant region. In addition to using consecutive bins that have a count parameter, embodiments can use other techniques, such as binary circular segmentation and Hidden Markov model, to identify a group of bins that correspond to an aberrant region. The bins can be merged to form a merged segment that corresponds to the aberrant region.

A. Merging Bins

As an example, the human genome is divided into non-overlapping bins using a window of a particular size. Examples of sizes of windows are 10 kb, 50 kb, 100 kb, 500 kb, and 1000 kb etc. In some embodiments, a bin with low mappability, for example less than 10%, is filtered out. An amount of DNA molecules can be determined for each bin, where a GC correction can be used to determine the amount from raw counts (Chen E Z et al. PLoS One. 2011; 6(7): e21791). The mappability corresponds to the ability to assign or identify reads originating from a region back to the true original genomic location by alignment. Some regions have low mappability, e.g., due to not enough unique nucleotide context. Such regions are under-represented in the sequencing depth.

The proportion of reads after GC correction (referred to as genomic representation, GR) aligned to bin i can be determined and referred to as $GR_i$. $GR_i$ can be further transformed to the z-score statistic for a testing sample, $Z_i$:

$$Z_i = \frac{GR_i - GR_{i0}}{SD_{i0}},$$

where $GR_{i0}$ and $SD_{i0}$ are the mean and standard deviation (SD) of GR corresponding to bin i in the group of healthy pregnancies carrying euploid fetuses (normal subjects), respectively.

A segmentation step can be then be applied to $Z_i$ along each chromosome. This segmentation step can merge consecutive bins exhibiting genomic representation changes in the same direction (e.g., relative overrepresentation, relative underrepresentation, or no change) into a larger segment, named as a merged segment. The segmentation can be performed in ascending or descending order of genomic coordinates. Various techniques can be used for the segmentation step.

In one embodiment, a binary circular segmentation and Hidden Markov model (bioconductor.org/packages/3.3/bioc/manuals/snapCGH/man/snapCGH.pdf) algorithm can be used to implement this segmentation step. A merged segment showing a positive z-score value that is statistically significantly elevated compared with the reference range established from unaffected controls or subjects can be identified as a candidate microduplication (or more generally as a microamplification). A merged segment showing a negative z-score value that is statistically significantly reduced compared with the reference range established from unaffected controls or subjects can be identified as a candidate microdeletion. The term "candidate" can refer to the region being a candidate for an aberration in the fetus, which can be confirmed using a size analysis.

A significant deviation from the normal range can be defined by more than just a threshold, e.g., as described in method 300. For example, a size of the merged segment can be analyzed to determine whether the merged segment is larger than a length threshold, e.g., at least 3 megabase (Mb). Examples of other length thresholds include 1 Mb, 2 Mb, 4 Mb, 5 Mb, 10 Mb etc.

Further, the magnitude of the deviation for the merged segment can be analyzed to determine whether the magnitude exceeds a deviation threshold. For instance, the absolute averaged z-score of the merged segment (i.e. including all bins in the merged segment) can be required to be greater than the deviation threshold (e.g., 1.5). Examples of other deviation thresholds include 1, 2, 3, 5, etc. The magnitude is an example of a count parameter or can be determined as part of a comparison of a count parameter to a count threshold, which could be the reference range. The averaged z-score can be an average of the individual z-scores or a z-score determined using a total amount of DNA molecules for the entire merged segment.

In some embodiments, an initial analysis of bins can be performed to identify aberrant bins that might form a merged segment that satisfies a length threshold and/or a deviation threshold. Such an initial analysis can also use a z-score analysis. A threshold for the initial analysis can be different (e.g., larger) than the deviation threshold used for the entire merged segment. Once a sufficient number of aberrant bins that are near each other (e.g. within a specified length, such as no gap less than 500 kb) are identified, the segmentation process can be used on bins in the area to identify a suitable region. Then, the region can be analyzed, e.g., using the length threshold and/or the deviation threshold. The length or the deviation can be tested separately to identify a candidate, or both can be required to be satisfied.

B. Aberration Containing Fraction (AcF)

As mentioned above, the aberration-containing fraction, can be used as a count parameter to determine a count classification of a type of aberration existing in the biological sample for the first subchromosomal region. Thus, the aberration-containing fraction can be used instead of a z-score of a region or an average z-score for bins of a region defined, e.g., by a merged segment. The aberration-containing fraction can thus be used as a deviation from the reference range of the merged segment. The aberration-containing fraction can correspond to the proportion of equivalent cells containing the aberrations in the sample.

The aberration-containing fraction can be defined in a variety of ways, e.g., using the definition in section IV, denoted as $F_{CNA}$. But, the aberration-containing fraction can be defined in other ways, here we denote as AcF.

In one embodiment, the AcF can be defined using the following equation:

$$AcF = \frac{|GR' - GR_0| \times 2 \times 100\%}{GR_0}$$

where GR' is GR of the merged segment (region) showing a microdeletion or microduplication in the test sample, and $GR_0$ is the mean GR of the merged segment in control (reference) samples.

In another embodiment, the AcF can be defined using the following equation:

$$\text{Or } AcF = |Z' \times CV_0| \times 2$$

where Z' is a z-score of the merged segment (region) showing microdeletion or microduplication in the test sample. $CV_0$ is the coefficient of variation (CV) of the corresponding region in normal subjects (also referred to as control or reference subjects or samples). In one embodiment, Z' of the merged segment was recalculated by comparing GR of the region in the test sample with the mean and standard deviation of GR of the corresponding region in normal subjects, e.g., according to z-score defined in section II.A. In another embodiment, Z' can be also estimated from a series of individual z-scores of bins falling within the merged segment by dividing the sum of 100-kb z-scores by the square root of the number of bins involved.

AcF can reflect the potential tissue of origin of aberrations. For example, if the aberration solely originated from the fetus, the AcF being would be equal to the fetal DNA fraction. If the aberrations solely originated from the mother, the AcF would be much greater than fetal DNA fraction because, in general, fetal DNA amounts to a minority proportion in plasma. If the aberration originated from both, the AcF being analyzed would be close to 100%.

Therefore, a separation value (e.g., a difference or a ratio) between AcF and the fetal DNA fraction can be used to classify the tissue of origin of the genomic aberrations seen in the sample. The fetal DNA fraction for a sample can be calculated using various techniques, such as SNP-based, size-based, and chrY-based approaches, e.g., as described in U.S. Patent Publication 2013/0237431.

Below are some examples for how the difference between AcF and the fetal DNA fraction can be used to infer if an aberration is originated from mother or fetus. For example, if the difference between AcF and the fetal DNA fraction is less than a low threshold (e.g., 2%), the aberration would be classified as "fetal-derived aberrations." Other examples of thresholds include 1%, 3%, 4%, and 5%.

If the difference between AcF and the fetal DNA fraction is greater than a high threshold (e.g., 20%), the aberration would be classified as "aberrations involving the mother." Other examples of high thresholds include 10%, 30%, 40%, and 50%. When the high threshold is exceeded, the aberration could be solely in the mother or both in the mother and fetus.

Because an aberration from the background maternal cells could be mosaic (i.e., only a proportion (<100%) of the maternal cells that contribute plasma DNA contain the aberration), the difference between the AcF and the fetal DNA fraction can have similar values when the aberrations are solely derived from the mother or both the mother and the fetus. In one embodiment, only a region showing AcF exceeding a certain threshold (e.g., 4%, 5%, 6%, etc.) may be considered as a candidate microdeletion or microduplication.

A first bin count parameter for a first bin of the first subchromosomal region can correspond to GR for the entire region, e.g., when the region has only one bin. A first score (AcF or $F_{CNA}$) for the region can be determined by subtracting the mean of the control bin count parameters from the first bin count parameter. In various embodiments, the result of the subtraction can be divided by the mean or the standard deviation of the control bin count parameters for normal subjects.

As described above, the fetal DNA concentration can be measured in the biological sample. A difference can be computed between the first score and the fetal DNA concentration. Determining whether the first score is greater than the cutoff value can include determining whether the difference is greater than a high threshold value, e.g., as described above. Further, the difference can be compared to a low threshold to determine that only the fetus has the aberration for the first subchromosomal region when the difference is below a low threshold value, e.g., as described above.

In embodiments where the first subchromosomal region includes a plurality of bins, a respective score can be computed for each of the plurality of bins. The first score can be determined using a sum of the respective scores. For example, an average can be taken. As another example, the first score is the sum divided by a square root of a number of bins used to determine the sum.

C. Results

Figure 9:
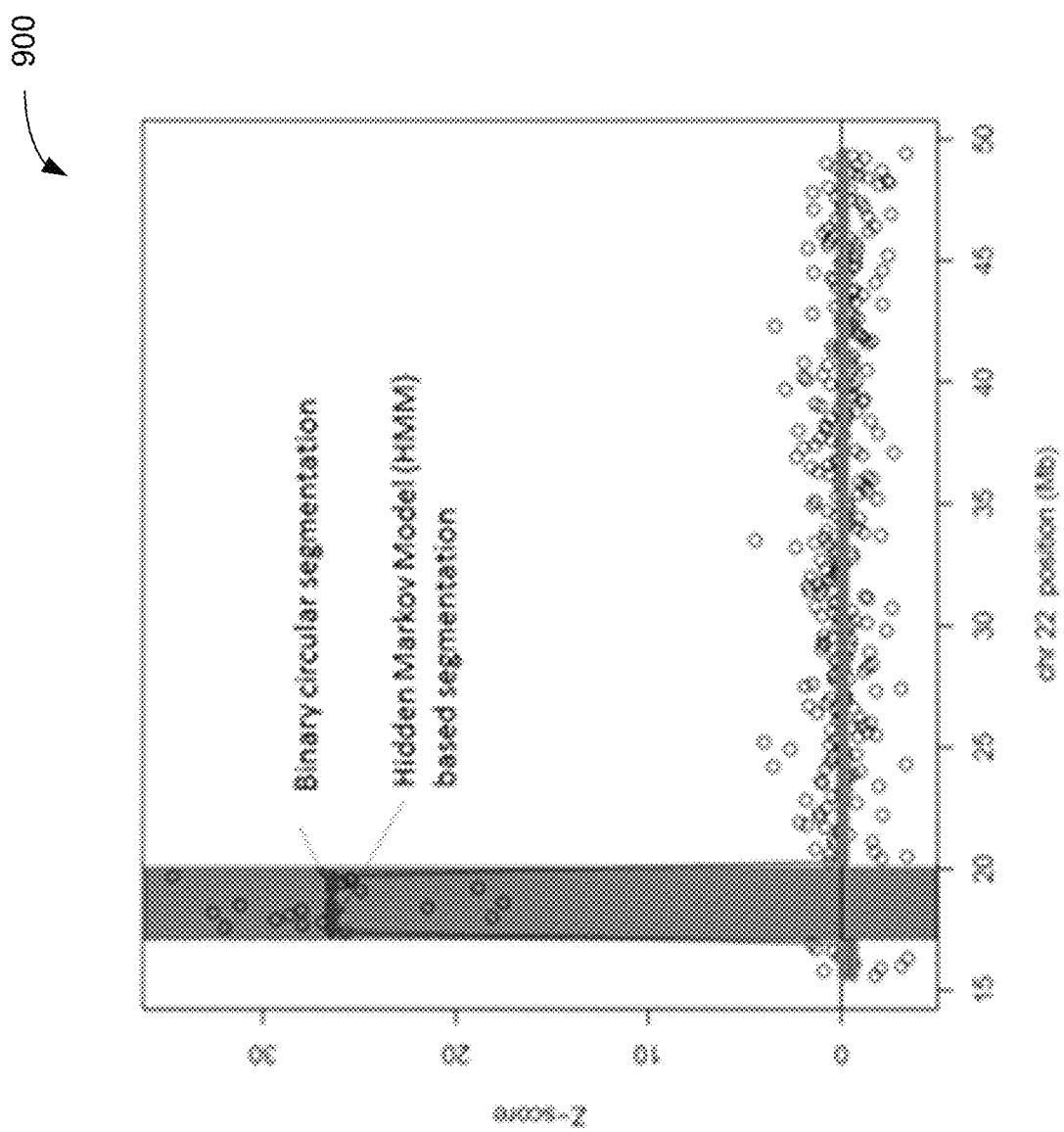
FIG. 9 is a plot 900 showing an amplified region composed of 100-kb bins determined by a segmentation process according to embodiments of the present invention.

FIG. 9 is a plot 900 showing an amplified region composed of 100-kb bins determined by a segmentation process according to embodiments of the present invention. Plot 900 provides an example of microduplication identification and integrated interpretation. Each chromosome was divided into 100-kb bins. In plot 900, each dot represents a z-score in a 100-kb bin.

Both binary circular segmentation and Hidden Markov Model (HMM) based segmentation were performed. In chromosome 22, both segmentation algorithms showed a consistent result. The merged segment (chr22: 17,000,000-20,000,000) as shown in the area of shaded region was identified as a candidate microduplication using the cutoff of size of the merged segment >3 Mb and the cutoff of the magnitude of the averaged z-score >1.5. The aberration-containing fraction (AcF) was determined to be 100% according to a count-based merged z-score of 72 for the merged segment.

The fetal DNA fraction was 22% using FetalQuant algorithm (Jiang P et al. Bioinformatics. 2012; 28(22):2883-90). AcF was much greater than the fetal DNA fraction, which indicated that mother's aberration would be present in this region. The size-based z-score was determined to be 0.9 for the merged region, suggesting a normal size distribution when compared with the cutoff of 3. Therefore, the size analysis suggested that the both mother and fetus would have microduplication in this region, per FIGS. 1 and 4. By comparing to a database, this candidate microduplication was found to be overlapped with 22q11 duplication syndrome.

Figure 10:
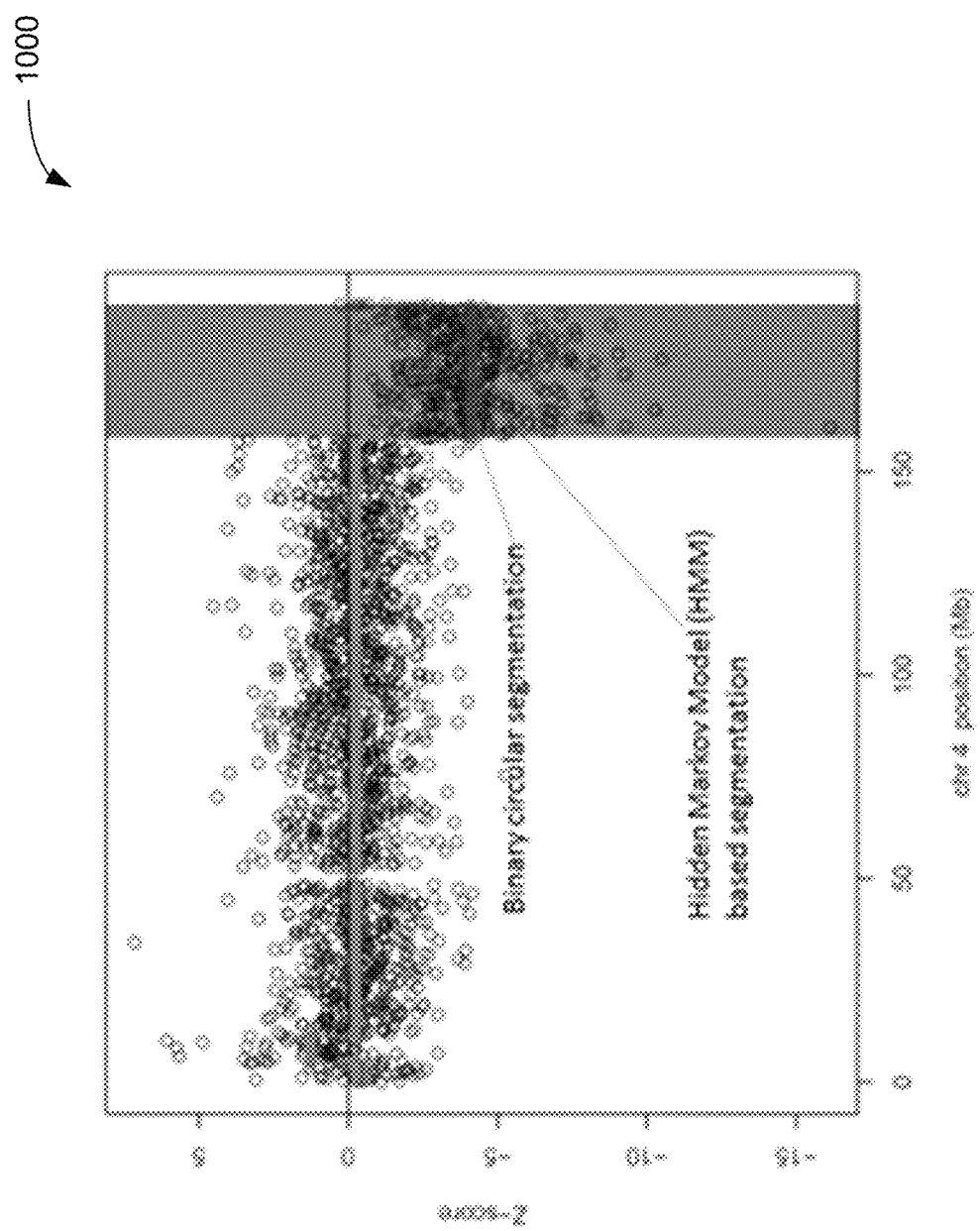
FIG. 10 is a plot 1000 showing a deleted region composed of 100-kb bins determined by a segmentation process according to embodiments of the present invention.

FIG. 10 is a plot 1000 showing a deleted region composed of 100-kb bins determined by a segmentation process according to embodiments of the present invention. Plot 1000 provides an example of microdeletion identification and integrated interpretation. Each chromosome was divided into 100-kb bins. In plot 1000, each dot represents a z-score in a 100-kb bin.

Both binary circular segmentation and Hidden Markov Model (HMM) based segmentation were performed. In chromosome 4, both segmentation algorithms showed a consistent result. The merged segment (chr4:158,000,000-198,000,000) as shown in the area of shaded region was identified as a candidate microdeletion using the cutoff of size of the merged segment >3 Mb and the magnitude of the averaged z-score >1.5. The aberration-containing fraction (AcF) was determined to be as 14.7% according to count-based merged z-score of −74.5 for the merged segment.

The fetal DNA fraction was 13% using FetalQuant algorithm (Jiang P et al. Bioinformatics. 2012; 28(22):2883-90). AcF was very close to the fetal DNA fraction (e.g., less than a low threshold of 2%), which indicated that only the fetus had the microdeletion present in this region. The size-based z-score was determined to be −14 for the merged segment, suggesting a significantly longer size distribution comparing with the cutoff of −3. Therefore, the size analysis suggested that the fetus would have a microdeletion in this region, per FIGS. 1 and 4.

VII. SUMMARY

Despite having a high detection rate and a low false-positive rate, NIPT for fetal subchromosomal aneuploidies using cell-free DNA in maternal plasma is currently not widely used as a screening test due to an insufficiently high positive predictive value. The positive predictive value of the test would be expected to be even lower if subchromosomal CNAs are included, as individual members of these conditions are even rarer than the whole chromosomal aneuploidies. In addition, the number of false positives due to multiple comparisons would increase as more targets are being tested. As reported by Yin et al., 20 of their 55 false-positive samples might be attributable to sequencing and statistical errors (12). As shown in embodiments of the present invention, a size-based analysis can serve as an independent method to confirm the aberration detected by the count-based analysis. The results show that one can minimize the number of false positives due to statistical errors with the combined count-based and size-based approach.

In some embodiments, to achieve a resolution of 2-Mb for the detection of fetal subchromosomal CNAs with a 95% sensitivity and a 99% specificity at a fetal DNA fraction of 5%, both the count-based and the size-based approaches would need to analyze around 200 million molecules (7). On the other hand, since the median fetal DNA fraction in the first trimester is approximately 15% (17,19), about 20 million molecules may be used to achieve the same performance. This estimation is based on the previously reported mathematical relationship whereby every two-fold increase in fetal DNA fraction would lead to a 4-fold decrease of molecules required for the same test performance (20). Since the same set of sequencing data can be used for both types of analyses, embodiments only requires additional reagent costs for the paired-end sequencing compared with the counting-only protocol that requires reagents for single-end sequencing. In addition, the time requirements for bioinformatics processing needed by the two protocols are comparable.

In summary, we have demonstrated that size analysis of plasma DNA in pregnant women can accurately detect fetal subchromosomal CNAs. The combined use of the size-based and count-based methods can further determine whether the fetus, the mother, or both of them carry the aberration. This combined approach is very valuable in helping clinicians to interpret the results of NIPT.

VIII. COMPUTER SYSTEM

Figure 11:
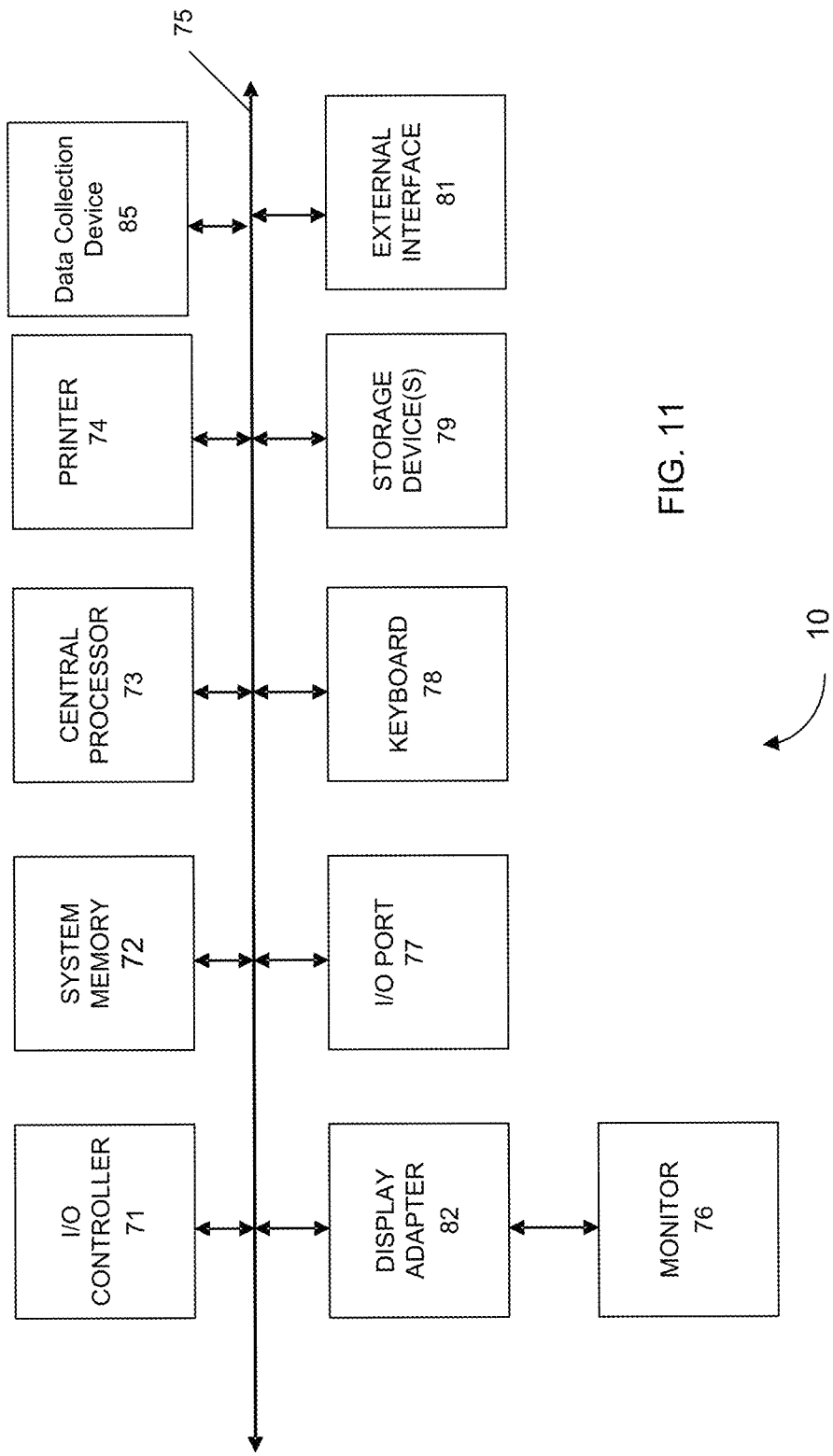
FIG. 11 shows a block diagram of an example computer system 10 usable with system and methods according to embodiments of the present invention.

Any of the computer systems mentioned herein may utilize any suitable number of subsystems. Examples of such subsystems are shown in FIG. 11 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 11 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

IX. REFERENCES

1. Bianchi D W, Wilkins-Haug L. Integration of noninvasive DNA testing for aneuploidy into prenatal care: What has happened since the rubber met the road? Clin Chem 2014; 60:78-87.
2. Wong F C K, Lo Y M D. Prenatal diagnosis innovation: Genome sequencing of maternal plasma. [Epub ahead of print] Annu Rev Med Oct. 15, 2015 as doi:10.1146/annurev-med-091014-115715.
3. Chiu RWK, Cantor C R, Lo YMD. Non-invasive prenatal diagnosis by single molecule counting technologies. Trends Genet 2009; 25:324-31.

4. Peters D, Chu T, Yatsenko S A, Hendrix N, Hogge W A, Surti U, et al. Noninvasive prenatal diagnosis of a fetal microdeletion syndrome. N Engl J Med 2011; 365:1847-8.
5. Jensen T J, Dzakula Z, Deciu C, van den Boom D, Ehrich M. Detection of microdeletion 22q11.2 in a fetus by next-generation sequencing of maternal plasma. Clin Chem 2012; 58:1148-51.
6. Srinivasan A, Bianchi D W, Huang H, Sehnert A J, Rava R P. Noninvasive detection of fetal subchromosome abnormalities via deep sequencing of maternal plasma. Am J Hum Genet 2013; 92:167-76.
7. Yu S C Y, Jiang P, Choy K W, Chan K C A, Won H-S, Leung W C, et al. Noninvasive prenatal molecular karyotyping from maternal plasma. PLoS ONE 2013; 8:e60968.
8. Zhao C, Tynan J, Ehrich M, Hannum G, McCullough R, Saldivar J-S, et al. Detection of fetal subchromosomal abnormalities by sequencing circulating cell-free DNA from maternal plasma. Clin Chem 2015; 61:608-16.
9. Hayden E C. Prenatal-screening companies expand scope of DNA tests. Nature 2014; 507:19-19.
10. Lau T K, Jiang F M, Stevenson R J, Lo T K, Chan L W, Chan M K, et al. Secondary findings from non-invasive prenatal testing for common fetal aneuploidies by whole genome sequencing as a clinical service. Prenat Diagn 2013; 33:602-8.
11. Snyder M W, Simmons L E, Kitzman J O, Coe B P, Henson J M, Daza R M, et al. Copy-number variation and false positive prenatal aneuploidy screening results. N Engl J Med 2015; 372:1639-45.
12. Yin A-H, Peng C-F, Zhao X, Caughey B A, Yang J-X, Liu J, et al. Noninvasive detection of fetal subchromosomal abnormalities by semiconductor sequencing of maternal plasma DNA. Proc Natl Acad Sci USA 2015; 112: 14670-5.
13. Yu S C Y, Chan K C A, Zheng Y W L, Jiang P, Liao G J W, Sun H, et al. Size-based molecular diagnostics using plasma DNA for noninvasive prenatal testing. Proc Natl Acad Sci USA 2014; 111:8583-8.
14. Chan K C A, Zhang J, Hui A B Y, Wong N, Lau T K, Leung T N, et al. Size distributions of maternal and fetal DNA in maternal plasma. Clin Chem 2004; 50:88-92.
15. Lo Y M D, Chan K C A, Sun H, Chen E Z, Jiang P, Lun F M F, et al. Maternal plasma DNA sequencing reveals the genome-wide genetic and mutational profile of the fetus. Sci Transl Med 2010; 2:61ra91.
16. Chiu R W K, Chan K C A, Gao Y, Lau V Y M, Zheng W, Leung T Y, et al. Noninvasive prenatal diagnosis of fetal chromosomal aneuploidy by massively parallel genomic sequencing of DNA in maternal plasma. Proc Natl Acad Sci USA 2008; 105:20458-63.
17. Chiu R W K, Akolekar R, Zheng Y W L, Leung T Y, Sun H, Chan K C A, et al. Non-invasive prenatal assessment of trisomy 21 by multiplexed maternal plasma DNA sequencing: large scale validity study. BMJ 2011; 342:c7401.
18. Palomaki G E, Kloza E M M, Lambert-Messerlian G M, Haddow J E, Neveux L M, Ehrich M, et al. DNA sequencing of maternal plasma to detect Down syndrome: An international clinical validation study. Genet Med 2011; 13:913-20.
19. Hudecova I, Sahota D, Heung M M S, Jin Y, Lee W S, Leung T Y, et al. Maternal plasma fetal DNA fractions in pregnancies with low and high risks for fetal chromosomal aneuploidies. PLoS ONE 2014; 9:e88484.
20. Lo YMD, Lun F M F, Chan K C A, Tsui N B Y, Chong K C, Lau T K, et al. Digital PCR for the molecular detection of fetal chromosomal aneuploidy. Proc Natl Acad Sci USA 2007; 104:13116-21.

What is claimed is:

1. A method of identifying a subchromosomal copy number aberration in a fetal genome of a fetus by analyzing a biological sample from a female subject pregnant with the fetus, the biological sample including cell-free DNA molecules from the female subject and the fetus, the method comprising:
for each of a plurality of DNA molecules in the biological sample:
identifying a location of the DNA molecule in a reference genome, thereby obtaining locations of the plurality of DNA molecules;
for each of a plurality of non-overlapping bins in the reference genome:
measuring a respective amount of the plurality of DNA molecules located in a respective non-overlapping bin using the locations of the plurality of DNA molecules,
computing a respective bin count parameter from the respective amount, and
comparing the respective bin count parameter to one or more bin count thresholds to determine a bin count classification of the respective non-overlapping bin;
performing, using a computer system, a segmentation process that merges consecutive non-overlapping bins into a merged segment based on the consecutive non-overlapping bins having a same bin count classification;
comparing a length of the merged segment to a length threshold;
computing a count parameter for the merged segment from bin count parameters of the non-overlapping bins of the merged segment or from amounts of the plurality of DNA molecules located in the non-overlapping bins of the merged segment;
comparing the count parameter to one or more deviation thresholds to determine a count classification;
classifying the fetus at risk of having the aberration in a subchromosomal region corresponding to the merged segment based on the comparison of the length of the merged segment to the length threshold and the count classification; and
testing the fetus to confirm the subchromosomal copy number aberration.

2. The method of claim 1, wherein the segmentation process includes at least one of: a binary circular segmentation and a Hidden Markov model.

3. The method of claim 1, wherein the bin count classification is over-represented or under-represented.

4. The method of claim 1, wherein the aberration is a deletion or a duplication.

5. The method of claim 1, wherein the fetus is determined to have an amplification in the subchromosomal region when the count parameter is greater than a deviation threshold of the one or more deviation thresholds.

6. The method of claim 1, wherein the fetus is determined to have a deletion in the subchromosomal region when the count parameter is less than a deviation threshold of the one or more deviation thresholds.

7. The method of claim 1, wherein the non-overlapping bins are of an equal size.

8. The method of claim 1, wherein the non-overlapping bins exclude bins with a mappability less than a predetermined percentage.

9. The method of claim 1, wherein measuring the respective amount comprises using a GC correction.

10. The method of claim 1, wherein computing the respective bin count parameter comprises calculating a z-score, and wherein the z-score comprises using an amount determined from a group of healthy pregnancies carrying euploid fetuses.

11. The method of claim 1, wherein the one or more bin count thresholds are greater than a deviation threshold of the one or more deviation thresholds.

12. The method of claim 1, wherein the count parameter for the merged segment is from the amounts of the plurality of DNA molecules located in the non-overlapping bins of the merged segment.

13. The method of claim 12, further comprising:
determining that the fetus and the female subject have the aberration when the count parameter is above a deviation threshold of the one or more deviation thresholds.

14. The method of claim 12, further comprising:
determining a fetal DNA fraction in the biological sample, and
determining the one or more deviation thresholds using the fetal DNA fraction.

15. The method of claim 14, further comprising:
comparing the count parameter to a first deviation threshold and a second deviation threshold of the one or more deviation thresholds, and
when the count parameter is greater than the first deviation threshold and less than the second deviation threshold:
determining the fetus has the aberration, and
determining the female subject does not have the aberration.

16. The method of claim 14, further comprising:
comparing the count parameter to a first deviation threshold and a second deviation threshold of the one or more deviation thresholds, and
when the count parameter is greater than the first deviation threshold and greater than the second deviation threshold:
determining the female subject has the aberration.

17. A computer product comprising a computer readable medium storing a plurality of instructions that when executed control a computer system to perform a method of identifying a subchromosomal copy number aberration in a fetal genome of a fetus, the method comprising:
for each of a plurality of DNA molecules in a biological sample from a female subject pregnant with the fetus, the biological sample including cell-free DNA molecules from the female subject and the fetus:
identifying a location of the DNA molecule in a reference genome, thereby obtaining locations of the plurality of DNA molecules;
for each of a plurality of non-overlapping bins in the reference genome:
measuring a respective amount of the plurality of DNA molecules located in a respective non-overlapping bin using the locations of the plurality of DNA molecules,
computing a respective bin count parameter from the respective amount, and
comparing the respective bin count parameter to one or more bin count thresholds to determine a bin count classification of the respective non-overlapping bin;
performing a segmentation process that merges consecutive non-overlapping bins into a merged segment based on the consecutive non-overlapping bins having a same bin count classification;
comparing a length of the merged segment to a length threshold;
computing a count parameter for the merged segment from bin count parameters of the non-overlapping bins of the merged segment or from amounts of the plurality of DNA molecules located in the non-overlapping bins of the merged segment;
comparing the count parameter to one or more deviation thresholds to determine a count classification;
classifying the fetus at risk of having a copy number aberration in a subchromosomal region corresponding to the merged segment based on the comparison of the length of the merged segment to the length threshold and the count classification; and
testing the fetus to confirm the subchromosomal copy number aberration.

18. The method of claim 1, wherein the plurality of DNA molecules comprises at least 20 million molecules.

19. The method of claim 1, wherein the reference genome is a human reference genome.

20. The method of claim 1, further comprising:
determining, by the computer system, a size classification for the merged segment by:
calculating a first statistical value of sizes of DNA molecules located in the merged segment;
calculating a reference statistical value of sizes of DNA molecules located in a reference region;
determining a separation value between the first statistical value and the reference statistical value; and
comparing the separation value to one or more size thresholds to obtain the size classification;
wherein determining whether the fetus has the aberration in the subchromosomal region corresponding to the merged segment is further based on the size classification.

21. A method of identifying a subchromosomal copy number aberration in a fetal genome of a fetus by analyzing a biological sample from a female subject pregnant with the fetus, the biological sample including cell-free DNA molecules from the female subject and the fetus, the method comprising:
for each of a plurality of DNA molecules in the biological sample:
identifying a location of the DNA molecule in a reference genome by hybridizing the DNA molecule to a panel of probes with known chromosomal origin, thereby obtaining locations of the plurality of DNA molecules;
for each of a plurality of non-overlapping bins in the reference genome:
measuring a respective amount of the plurality of DNA molecules located in a respective non-overlapping bin using the locations of the plurality of DNA molecules,
computing a respective bin count parameter from the respective amount, and
comparing the respective bin count parameter to one or more bin count thresholds to determine a bin count classification of the respective non-overlapping bin;

performing, using a computer system, a segmentation process that merges consecutive non-overlapping bins into a merged segment based on the consecutive non-overlapping bins having a same bin count classification;

comparing a length of the merged segment to a length threshold;

computing a count parameter for the merged segment from bin count parameters of the non-overlapping bins of the merged segment or from amounts of the plurality of DNA molecules located in the non-overlapping bins of the merged segment;

comparing the count parameter to one or more deviation thresholds to determine a count classification;

classifying the fetus at risk of having the aberration in a subchromosomal region corresponding to the merged segment based on the comparison of the length of the merged segment to the length threshold and the count classification; and testing the fetus to confirm the subchromosomal copy number aberration.

22. The computer product of claim 17, wherein each bin of the plurality of non-overlapping bins has a size from 500 kb to 2 Mb.

* * * * *